US008852127B2

United States Patent
Bell et al.

(10) Patent No.: US 8,852,127 B2
(45) Date of Patent: Oct. 7, 2014

(54) SYSTEM AND METHOD FOR MONITORING INFORMATION RELATED TO SLEEP

(75) Inventors: Florian G. Bell, Bend, OR (US); Donna K. Barton, Bend, OR (US); Charles A. Czeisler, Sherborn, MA (US)

(73) Assignee: Ric Investments, LLC, Wilmington, DE (US)

( * ) Notice: Subject to any disclaimer, the term of this patent is extended or adjusted under 35 U.S.C. 154(b) by 1549 days.

(21) Appl. No.: 12/131,220

(22) Filed: Jun. 2, 2008

(65) Prior Publication Data

US 2008/0319354 A1 Dec. 25, 2008

Related U.S. Application Data

(60) Provisional application No. 60/942,935, filed on Jun. 8, 2007.

(51) Int. Cl.
| | |
|---|---|
| A61B 5/103 | (2006.01) |
| A61B 5/117 | (2006.01) |
| A61B 5/04 | (2006.01) |
| G08B 23/00 | (2006.01) |
| G01J 1/42 | (2006.01) |
| G01J 3/51 | (2006.01) |
| A61B 5/00 | (2006.01) |
| A61B 5/11 | (2006.01) |
| G01J 1/02 | (2006.01) |
| G01J 1/04 | (2006.01) |

(52) U.S. Cl.
CPC .............. *A61B 5/11* (2013.01); *G01J 1/4204* (2013.01); *G01J 1/0488* (2013.01); *G01J 3/513* (2013.01); *A61B 2560/0456* (2013.01); *A61B 2560/0242* (2013.01); *A61B 5/4812* (2013.01); *A61B 5/4809* (2013.01); *G01J 1/0247* (2013.01); *G01J 1/0233* (2013.01); *A61B 5/7232* (2013.01); *A61B 5/681* (2013.01)
USPC ........ 600/587; 600/544; 600/595; 340/573.1; 340/575

(58) Field of Classification Search
USPC ................ 600/587, 595, 544, 476; 340/573.1
See application file for complete search history.

(56) References Cited

U.S. PATENT DOCUMENTS

| | | | | |
|---|---|---|---|---|
| 5,140,562 | A | * 8/1992 | Moore-Ede et al. | ............ 368/62 |
| 5,973,417 | A | 10/1999 | Goetz et al. | |

(Continued)

FOREIGN PATENT DOCUMENTS

| | | |
|---|---|---|
| JP | 6141929 A | 2/1986 |
| JP | 10246672 A | 9/1998 |

(Continued)

OTHER PUBLICATIONS

Berlien, J., Intelligent Opto Sensor Designer's Notebook, Color Classification with the TCS230 Identifying and Sorting Colors by Hue, Mar. 4, 2004, pp. 1-7, No. 11, TAOS, Inc.

(Continued)

*Primary Examiner* — Devin Henson

(57) ABSTRACT

A system configured to monitor ambient illumination experienced by a subject. In one embodiment, the system comprises an illumination sensor, a timer, and a storage module. The illumination sensor is configured to monitor an intensity of ambient illumination within two or more wavelength ranges by generating one or more output signals that convey information related to the intensity of ambient illumination within the two or more wavelength ranges. The timer is configured to indicate the passage of periods of time. The storage module is configured to store information related to the intensity of ambient illumination within the two or more wavelength ranges, as conveyed by the one or more output signals, for individual periods of time. The system is portable to be carried by the subject.

16 Claims, 11 Drawing Sheets

(56) References Cited

U.S. PATENT DOCUMENTS

| | | | |
|---|---|---|---|
| 5,978,606 | A | 11/1999 | Ishikawa |
| 6,518,820 | B2 | 2/2003 | Gremm |
| 6,522,078 | B1 | 2/2003 | Okamoto et al. |
| 2004/0089810 | A1 | 5/2004 | Brown et al. |
| 2005/0029456 | A1 | 2/2005 | Eggers et al. |
| 2006/0224047 | A1* | 10/2006 | Suzuki et al. ............. 600/300 |
| 2007/0268363 | A1* | 11/2007 | Raskar et al. ............. 348/135 |
| 2008/0146958 | A1* | 6/2008 | Guillory et al. ............. 600/544 |
| 2010/0174345 | A1* | 7/2010 | Ashdown ............. 607/88 |

FOREIGN PATENT DOCUMENTS

| | | |
|---|---|---|
| JP | 2000294386 A | 10/2000 |
| JP | 2006271897 A | 10/2006 |
| WO | 2005066868 A3 | 7/2005 |
| WO | 2007072412 A2 | 6/2007 |
| WO | 2009045235 A2 | 4/2009 |

OTHER PUBLICATIONS

Poynton, C., Sensing color with the TAOS TCS230, May 17, 2005, pp. 1-15, TAOS, Inc.

Quantum Research Group, Secrets of a Successful QTouch™ Design, Oct. 2005, pp. 1-11.

Imagine Tools, General Topic: Analog Sensors Specific Use: Capacitive Proximity Sensor, No date available, pp. 1-9.

Allen-Bradley, Capacitive Proximity Sensors, No date available, pp. 4-1 and 4-2.

\* cited by examiner

SYSTEM AND METHOD FOR MONITORING INFORMATION RELATED TO SLEEP

CROSS-REFERENCE TO RELATED APPLICATIONS

This application claims priority under 35 U.S.C. §119(e) from provisional U.S. Patent Application No. 60/942,935 filed Jun. 8, 2007, the contents of which are incorporated herein by reference

BACKGROUND OF THE INVENTION

1. Field of the Invention

The invention relates to systems and methods for determining information related to the context and/or physiological function of a subject to determine information related to the sleep of the subject.

2. Description of the Related Art

Systems for determining information related to the context and/or physiological function of a subject are known. Some of these systems include devices that are portable and/or wearable by the subject and enable the subject to be monitored throughout her ordinary day. However, conventional systems do not monitor various aspects of the subject's context that may enable an enhanced determination of information related to the circadian phase of the subject. The contextual information may be monitored by one or more sensors that have inherent inaccuracies that are not corrected for in known systems. Further, information storage by portable and/or wearable devices may be in conventional systems may be inefficient, which requires bulkier devices to store additional information.

SUMMARY OF THE INVENTION

One aspect of the invention relates to a system configured to monitor ambient illumination experienced by a subject. In one embodiment, the system comprises an illumination sensor, a timer, and a storage module. The illumination sensor is configured to monitor an intensity of ambient illumination within two or more wavelength ranges by generating one or more output signals that convey information related to the intensity of ambient illumination within the two or more wavelength ranges. The timer is configured to indicate the passage of periods of time. The storage module is configured to store information related to the intensity of ambient illumination within the two or more wavelength ranges, as conveyed by the one or more output signals, for individual periods of time. The system is portable to be carried by the subject.

Another aspect of the invention relates to a method of monitoring ambient illumination experienced by a subject. In one embodiment, the method comprises monitoring an intensity of ambient illumination within two or more wavelength ranges with an illumination sensor carried by the subject; determining the passage of periods of time; and storing the information related to the intensity of ambient illumination within the two or more wavelength ranges for individual periods of time.

Another aspect of the invention relates to a system configured to monitor ambient illumination experienced by a subject. In one embodiment, the system comprises means for monitoring an intensity of ambient illumination within two or more wavelength ranges by generating one or more output signals that convey information related to the intensity of ambient illumination within the two or more wavelength ranges; means for determining the passage of periods of time; and means for storing information related to the intensity of ambient illumination within the two or more wavelength ranges, as conveyed by the one or more output signals, for individual periods of time. The system is portable to be carried by the subject.

Another aspect of the invention relates to a system configured to determine information related to ambient illumination experienced by a subject. In one embodiment, the system comprises a receiver, and a processor. The receiver is configured to receive information related to (i) an intensity of ambient illumination experienced by the subject within two or more wavelength ranges, and (ii) an overall intensity of ambient illumination experienced by the subject. The processor is configured to determine a score that represents the resetting effect of the ambient illumination experienced by the subject on the circadian phase of the subject based on the intensity of the ambient illumination experienced by the subject within the two or more wavelength ranges and the overall intensity of ambient illumination experienced by the subject.

Another aspect of the invention relates to a method of determining information related to ambient illumination experienced by a subject. In one embodiment, the method comprises obtaining information related to an intensity of ambient illumination experienced by the subject within two or more wavelength ranges; obtaining information related to an overall intensity of ambient illumination experienced by the subject; and determining a score that represents the resetting effect of the ambient illumination experienced by the subject on the circadian phase of the subject based on the intensity of the ambient illumination experienced by the subject within the two or more wavelength ranges and the overall intensity of ambient illumination experienced by the subject.

Another aspect of the invention relates to a system configured to determine information related to ambient illumination experienced by a subject. In one embodiment the system comprises means for obtaining information related to an intensity of ambient illumination experienced by the subject within two or more wavelength ranges; means for obtaining information related to an overall intensity of ambient illumination experienced by the subject; and means for determining a score that represents the resetting effect of the ambient illumination experienced by the subject on the circadian phase of the subject based on the intensity of the ambient illumination experienced by the subject within the two or more wavelength ranges and the overall intensity of ambient illumination experienced by the subject.

Another aspect of the invention relates to a system configured to store information related to the context and/or physiological function of a subject. In one embodiment, the system comprises a sensor, a timer, a processor, and a storage module. The sensor is configured to monitor a parameter by generating one or more output signals that convey information related to the parameter, wherein the parameter is related to an ambient condition experienced by the subject or a physiological function of the subject. The timer is configured to indicate the passage of periods of time. The processor is configured to receive the one or more output signals generated by the sensor, to determine a value of the parameter for individual periods of time for storage, and to compress the determined values of the parameter for individual periods of time by expressing a series of periods, proximate in time to each other, for which the parameter remains at a similar value as a value that is representative of the values for the series of periods and the number of periods in the series of periods. The storage module is operatively connected to the processor, and is configured to store compressed information provided by the processor.

Another aspect of the invention relates to a method of storing information related to the context and/or the physiological function of a subject. In one embodiment, the method comprises obtaining one or more output signals that convey information related to a parameter, wherein the parameter is related to an ambient condition experienced by the subject or a physiological function of the subject; determining the passage of periods of time; determining a value of the parameter for individual periods of time for storage; compressing the determined values of the parameter for individual periods of time by expressing a series of periods, proximate in time to each other, for which the parameter remains at a similar value as a value that is representative of the values for the series of periods and the number of periods in the series of periods; and storing the compressed information.

Another aspect of the invention relates to a system configured to store information related to the context and/or physiological function of a subject. In one embodiment, the system comprises means for obtaining one or more output signals that convey information related to the parameter, wherein the parameter is related to an ambient condition experienced by the subject or a physiological function of the subject; means for determining the passage of periods of time; means for determining a value of the parameter for individual periods of time for storage based on the obtained one or more output signals; means for compressing the determined values of the parameter for individual periods of time by expressing a series of periods, proximate in time to each other, for which the parameter remains at a similar value as a value that is representative of the values for the series of periods and the number of periods in the series of periods; and means, operatively connected to the means for compressing, for storing the compressed information.

Another aspect of the invention a method of correcting for an overlap in the wavelength responses of a first illumination sensor and a second illumination sensor. In one embodiment, the method comprises providing illumination that has a smoothly varying wavelength over the wavelength responses of the first illumination sensor and the second wavelength sensor; filtering the provided illumination with a first filter having a transmission function that corresponds to the wavelength response of the first illumination sensor; measuring the total irradiance of the illumination that has been filtered by the first filter; filtering the provided illumination with a second filter having a transmission function that corresponds to the wavelength response of the second illumination sensor; measuring the total irradiance of the illumination that has been filtered by the second filter; filtering the provided illumination with both the first and the second filters; measuring the total irradiance of the illumination that has been filtered by the first and the second filter; and determining a correction for an overlap between the wavelength responses of the first and the second illumination sensors based on the measured irradiances.

Another embodiment of the invention relates to a system configured to correct for overlapping wavelength response functions of illumination sensors. In one embodiment, the system comprises a processor and a storage module. The processor is configured to obtain information related to one or more output signals that convey information related to the intensity of ambient illumination within two or more wavelength ranges, and to determine an illumination source type of an illumination source emitting the ambient illumination based on one or more comparisons between the intensities of the ambient illumination within individual ones of the two or more wavelength ranges. The storage module stores corrections corresponding to a plurality of illumination source types. The processor is further configured to access the correction stored in the storage module that corresponds to the illumination source type determined from the information related to the one or more output signals, and to implement the accessed correction in determining the intensities of the ambient illumination within the two or more wavelength ranges based on the information related to the one or more output signals.

Another aspect of the invention relates to a method of correcting for overlapping wavelength response functions of illumination sensors. In one embodiment, the method comprises obtaining information related to one or more output signals that convey information related to the intensity of ambient illumination within two or more wavelength ranges; determining an illumination source type of an illumination source emitting the ambient illumination based on one or more comparisons between the intensities of the ambient illumination within individual ones of the two or more wavelength ranges; accessing a correction from a set of stored corrections that correspond to a plurality of illumination source types, the accessed correction corresponding to the determined illumination source type; and implementing the accessed correction in determining the intensities of the ambient illumination within the two or more wavelength ranges based on the information related to the one or more output signals.

Another aspect of the invention relates to a system configured to correct for overlapping wavelength response functions of illumination sensors. In one embodiment, the system comprises means for obtaining information related to one or more output signals that convey information related to the intensity of ambient illumination within two or more wavelength ranges; means for determining an illumination source type of an illumination source emitting the ambient illumination based on one or more comparisons between the intensities of the ambient illumination within individual ones of the two or more wavelength ranges; means for accessing a correction from a set of previously stored corrections that correspond to a plurality of illumination source types, the accessed correction corresponding to the determined illumination source type; and means for implementing the accessed correction in determining the intensities of the ambient illumination within the two or more wavelength ranges based on the information related to the one or more output signals.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
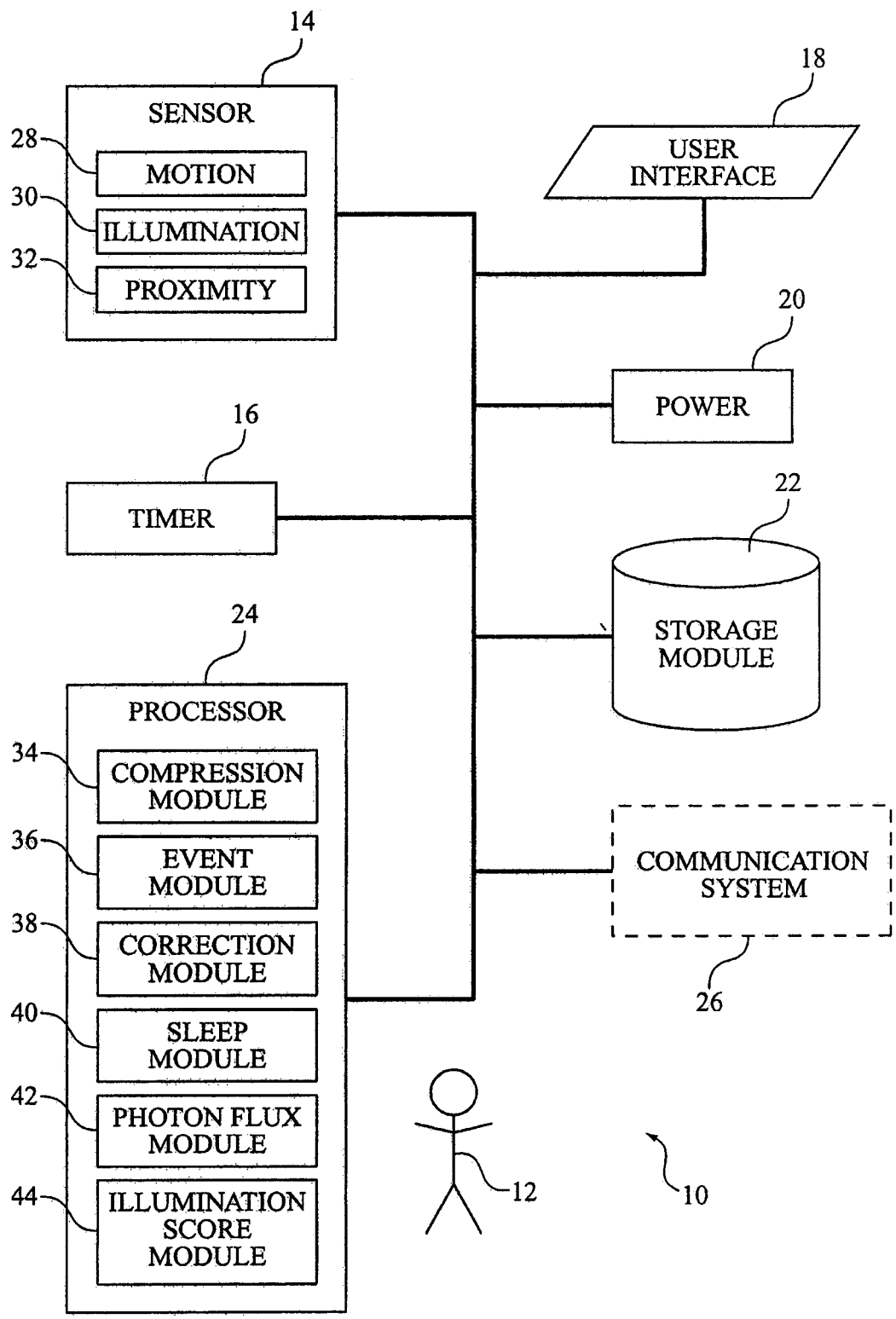
FIG. 1 illustrates a system configured to determine information related to the context and/or physiological function of a subject, according to one embodiment of the invention.

FIG. 1 is a schematic representation of one embodiment of a system 10 configured to determine information related to the context and/or physiological function of a subject 12. In particular, the information determined by system 10 is related to the sleep cycles and/or circadian phases of subject. For example, in one embodiment, system 10 may determine information related to the body movement of subject 12, ambient illumination experienced by subject 12, and/or other information related to the context and/or physiological function of subject 12. In one embodiment, system 10 includes a sensor 14, a timer 16, a user interface 18, a power module 20, a storage module 22, and a processor 24. In some implementations, system 10 may further include a communication system 26 that enables operative communication between the components of system 26 (e.g., sensor 14, timer 16, user interface 18, power module 20, storage module 22, processor 24, etc.), and/or between sub-components of the components of system 10 that are located remotely from each other.

Sensor 14 is configured to monitor one or more physiological functions of subject 12 and/or one or more ambient conditions experienced by subject 12. In one embodiment, sensor 14 further monitors one or more aspects of the use of sensor 14 to ensure that information gathered by sensor 14 will be accurate. More particularly, sensor 14 includes one or more sensor devices that generate one or more output signals conveying information related to the one or more physiological functions, the one or more ambient conditions, and/or the one or more aspects of the use of sensor 14. For example, in one embodiment, sensor 14 includes a motion sensor 28, an illumination sensor 30, and a proximity sensor 32. It should be appreciated that this listing of the sensor devices included in sensor 14 is not intended to be limiting, and that sensor 14 may be included with other sensor devices and/or without all of the listed sensor devices. Further, although sensor 14 is shown in FIG. 1 as combining the included sensor devices (sensors 28, 30, and 32) into a single, discrete element of system 10, this is for illustrative purposes only. Sensor devices 28, 30, and 32 may be located separately from each other and/or function distinctly from each other in fulfilling their functions within system 10.

Motion sensor 28 is configured to monitor movement of subject 12 by generating an output signal that conveys information about the movement of subject 12. As is discussed further below (e.g., with respect to FIG. 2), in one embodiment, portions of system 10 illustrated in FIG. 1 are provided in a device that is portable to be carried by subject 12, and may even be wearable by subject 12. In this embodiment, motion sensor 28 can be implemented as a sensor that is mounted on subject 12 to move with subject 12, and to generate an output signal that conveys information about the motion of motion sensor 28 with subject 12. For example, motion sensor 28 may be mounted on an extremity of subject 12 (e.g., the wrist of subject 12), and monitor the movement of the extremity. In such an embodiment, motion sensor 28 may include an actimeter, a position sensor, a displacement sensor, an accelerometer, and/or other sensors capable of monitoring motion and/or position.

According to various embodiments, motion sensor 28 includes a piezo-electric sensor that generates an output voltage in response to deformation produced by changes in motion (i.e., acceleration). In one such embodiment, the motion sensor 28 includes a type of piezo-electric sensor typically implemented in circumstances that require detection of relatively extreme changes in motion (in comparison with typical body movement) such as automobile airbags. These sensors are commonly referred to as "shock sensors," and include a piezo-electric element enclosed in a miniature ceramic package that can be mounted directly to a circuit board. Since, these elements are designed for detection of relatively extreme changes in motion, in an embodiment including a shock sensor as the piezo-electric element, motion sensor 28 further includes a drive circuit that is designed to provide the proper sensitivity such that typical human movements can be accurately monitored.

Illumination sensor 30 is configured to monitor ambient illumination experienced by subject 12. In one embodiment sensor 30 monitors the intensity of ambient illumination within two or more wavelength ranges by generating one or more output signals that convey information related to the intensity of ambient illumination in the two or more wavelength ranges. In one embodiment, the two or more wavelength ranges include three wavelength ranges. The three wavelength ranges may be selected such that virtually any color in the visible spectrum may be represented by a combination of illumination from the three wavelength ranges. For instance, the three wavelength ranges may include a wavelength range corresponding to red, a wavelength range corresponding to green, and a wavelength range corresponding to blue.

In one embodiment, illumination sensor 30 includes an integrated array of miniature optical sensors (e.g., photodiodes) that are arranged onto a substrate. The optical sensors include three sets of optical sensors that correspond to three wavelength ranges in which illumination is measured by the optical sensors. An address line enables each of the sensor groups to be activated and read out (separately or simultaneously). When a given one of the sensor groups is activated, the illumination sensor outputs an output signal that indicates the irradiance (watts/cm$^2$) of ambient light in the wavelength range that corresponds to the given sensor group.

In one embodiment, illumination sensor 30 includes a plurality of discrete photodiodes that correspond to individual ones of the wavelength ranges monitored by illumination sensor 30. For example, the photodiodes implemented may include wavelength-sensitive photodiodes ("WSPDs"). Each WSPD has a wavelength response function that describes its response to illumination with a given wavelength. The WSPDs are selected such that the wavelength response of a given WSPD implemented in illumination sensor 30 corresponds to one of the wavelength ranges to be monitored.

During use, in one embodiment, the WSPDs are individually activated in sequential order, and the output signal thereby generated provides a measurement of the intensity of ambient illumination in the individual wavelength regions. The output signal of illumination sensor 30 in volts is produced by coupling an activated WSPD, which generates a current proportional to the intensity of ambient illumination in the corresponding wavelength range, with a resistor, the voltage across the resistor being the output signal.

In one embodiment, the resistor that is connected in series with a given one of the WSPDs comprises a switchable set of resistors that can be selectively switched into and out of the circuit. This enables the load of the resistor to be varied so that at low ambient light intensity (with a corresponding low current produced by the given WSPD) the load can be increased to generate an output signal that will provide sensitivity at the relatively low light intensity. Similarly, at relatively high ambient light intensities, the load provided by the set of resistors can be reduced to avoid saturation of the output signal that would occur if the resistor's load was fixed, and designed to provide sensitivity at relatively low light intensity.

In one embodiment, illumination sensor 30 includes a spectrophotometer. The spectrophotometer is configured to provide one or more output signals that convey information related to the intensity of the two or more wavelength ranges of ambient illumination. This embodiment of illumination sensor 30 would typically be larger in size than the other embodiments described above. However, the implementation of a spectrophotometer, where the increased size is practical, may provide other enhancements with respect to the implementation of an array of photodiodes, or discrete photodiodes.

Proximity sensor 32 is configured to monitor the proximity of subject 12 to sensor 14. The proximity of subject 12 to sensor 14 ensures that ambient illumination monitored by illumination sensor 30 is the ambient illumination that is actually experienced. Further, the proximity of sensor 14 to subject 12 ensures that movement of subject 12 is accurately monitored by motion sensor 28. For instance, in an embodiment in which motion sensor 28 includes an accelerometer or other motion sensor to be worn on subject 12, if the "fit" of motion sensor 28 is loose, there may be motion of subject 12 that is not completely reflected in the output signal of motion sensor 28. Similarly, if motion sensor 28 is fitted loosely to subject 12, motion sensor 28 may move relative to subject 12 (e.g., slippage), and such movement would be reflected in the output signal of motion sensor 28 as movement of subject 12. Further, if subject 12 has removed sensor 14 from contact with herself, then none of the motion of subject 12 would be reflected in the output signal of motion sensor 28.

In one embodiment, discussed below with respect to FIG. 3, proximity sensor 32 includes a capacitive sensor that implements the dielectric properties of the anatomy of subject 12 to enable determination of whether sensor 14 is disposed proximate to subject 12. This may include determining whether sensor 14 has been removed from subject 12 during use, and in some instances may include detecting an improper fit of sensor 14 on subject 12 (e.g., a loose fit that enables relative movement therebetween).

Timer 16 is configured to indicate the passage of periods of time. In order to monitor the context and/or the physiological function of subject 12, information related to the context and/or physiological function may be processed and/or recorded for each of a set of discrete time periods sometimes referred to herein as epochs. For example, in the implementation of system 10 to determine information related to the circadian phases of subject 12, the periods may be anywhere from about one or more seconds to a few minutes (e.g., about 5 minutes) in length. Further, in one embodiment, periods of different length are simultaneously determined (e.g., one set of 3 second periods and one set of 10 second periods). This enables information related to different aspects of the context and/or the physiological function to be monitored with respect to periods of different duration (e.g., a first aspect is monitored with respect to the 3 second periods and the second aspect is monitored with respect to the 10 second aspects). In one embodiment, timer 16 includes an integrated circuit that provides electronic pulses indicating the passage of time. It should be appreciated that although timer 16 is illustrated in FIG. 1 as a discrete component of system 10, in one embodiment, some or all of the actual elements of timer 16 may be included integrally within processor 24.

User interface 18 is configured to provide an interface between system 10 and one or more users (e.g., a caregiver, a researcher, subject 12, etc.) through which users may provide information to and receive information from system 10. This enables data, results, and/or instructions and any other communicable items, collectively referred to as "information", to be communicated between the user(s) and one or more of sensor 14, timer 16, power module 20, storage module 22, and/or processor 24. Examples of conventional interface devices suitable for inclusion in user interface 18 include a keypad, buttons, switches, a keyboard, knobs, levers, a display screen, a touch screen, speakers, a microphone, an indicator light, an audible alarm, and a printer. In one embodiment, the functionality of which is discussed further below, user interface 18 actually includes a plurality of separate interfaces, including one interface that is provided in a device integral with sensor 14, and a separate interface provided to view and/or manage stored information that has been retrieved from the device integrated with sensor 14 (e.g., provided by a host computer to which information from sensor 14 and other accompanying components of system 10 can be received).

It is to be understood that other communication techniques, either hardwired or wireless, are also contemplated by the present invention as user interface 18. For example, the present invention contemplates that user interface 18 may be integrated with a removable storage interface provided by storage module 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

Power module 20 is configured to provide power to one or more of the other components of system 10. In one embodiment, power module 20 includes a rechargeable battery that provides regulated power to one or more of the other components of system 10. In this embodiment, power module 20 includes a recharging circuit that regulates the recharging of the battery when power module 20 is connected with an external power source (e.g., a wall socket, a host computer, etc.).

Storage module 22 provides electronic storage capabilities for system 10. Storage module 22 includes one or more electronically readable storage media that are operatively coupled with one or more of sensor 14, timer 16, user interface 18, processor 24, and/or communication system 26. This operative couple is illustrated in FIG. 1. The electronically readable storage media of storage module 22 may include one or both of system storage that is provided integrally (i.e., substantially non-removable) with system 10 and removable storage that is removably connectable to system 10 via, for example, a port (e.g., a USB port, a firewire port, etc.) or a drive (e.g., a disk drive, etc.). Storage module 22 may include one or more of optically readable storage media (e.g., optical disks, etc.), magnetically readable storage media (e.g., magnetic tape, magnetic hard drive, floppy drive, etc.), electrical charge-based storage media (e.g., BEPROM, RAM, etc.), solid-state storage media (e.g., flash drive, etc.), and/or other electronically readable storage media. Storage module 22 may store software algorithms, information related to the output signals generated by sensor 14 and/or timer 16, information determined by processor 24, and/or other information that enables system 10 to function properly. Storage module 22 may be a separate component within system 10, or storage module 22 may be provided integrally with one or more of sensor 14 or processor 24.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device, or processor 24 may represent processing functionality of a plurality of devices operating in coordination. For example, in one embodiment, the functionality attributed below to processor 24 is divided between a first processor that is operatively connected to sensor 14 in a device designed to be portable, or even wearable, by subject 12, and a second processor that communicates with the portable device at least periodically to obtain information related to the output signals generated by sensor 14 and further process the obtained information. In this embodiment, the second processor of processor 24 includes a processor provided by a host computer. Processors external to other components within system 10 (e.g., the second processor mentioned above) may, in some cases, provide redundant processing to the processors that are integrated with components in system 10 (e.g., the first processor mentioned above), and/or the external processor(s) may provide additional processing to determine additional information related to the operation of system 10 and/or the circadian phases of subject 12.

As is shown in FIG. 1, in one embodiment, processor 24 includes a compression module 34, an event module 36, a correction module 38, a sleep module 40, a photon flux module 42, and an illumination score module 44. Modules 34, 36, 38, 40, 42, and 44 may be implemented in software; hardware; firmware; some combination of software, hardware, and/or firmware; and/or otherwise implemented. It should be appreciated that although modules 34, 36, 38, 40, 42, and 44 are illustrated in FIG. 1 as being co-located within a single processing unit, in implementations in which processor 24 includes multiple processing units (e.g., the first processor disposed in the portable device and the second processor in at least periodic communication therewith), modules 34, 36, 38, 40, 42, and/or 44 may be located remotely from the other modules.

Compression module 34 is configured to compress information for storage within storage module 22. This compression is typically implemented in the embodiment in which system 10 includes the first and second processors described above, and enables the storage of information within storage module 22, which is also included in the portable device, while reducing the size of the information. Reducing the size of the information enables the size of storage module 22 to be reduced (both the physical size and the storage amount of storage space required), which in turn enhances the form factor of the portable device, and/or enables more information to be stored within storage module 22 without downloading the stored information from storage module 22 to the second processor for further processing.

In one embodiment, compression module 34 implements lossy and/or lossless compression. For example, analog output signals generated by sensor 14 may be converted to 16-bit digital signals, which may in turn be compressed by compression module 34 to 8-bits for storage. This would comprise a lossy compression. Another of a lossy compression is implemented in an embodiment in which compression module 34 implements the base 2 logarithm to compress a digital representation of one or more output signals generated by sensor 14. As another example, in one embodiment, compression module 34 receives representations (e.g., a digital representation of the analog value) of an output signal of sensor 14 (e.g., an output signal that conveys information related to motion, illumination intensity, etc.) for individual periods of time (as determined by timer 16), and compresses the representations by expressing a series of periods (i) that are proximate to each other in time, and (ii) for which the representations of the output signal have a similar value, as (a) a value representative of the representations of the output signal for the periods included in the series and (b) the number of periods included in the series of periods. This would comprise a lossless, or substantially lossless compression, depending on the requisite similarity of the values of the representations of the output signal for the series of periods.

Event module 36 is configured to determine information related to various events that can be determined based on the output signals generated by sensor 14. For example, an event may be detected based on the output signal(s) generated by proximity sensor 32. These events may include a removal of sensor 14 from subject 12 or a replacement of sensor 14 on subject 12 (subsequent to a removal). These events may be used to determine useful information generated by sensor 14 from information that may not be useful, due to the removal of sensor 14 from subject 12. In one embodiment in which system 10 includes the portable device with the first processor described briefly above, event module 36 is executed, at least in part, on the portable device to determine whether sensor 14 is properly installed on subject 12. In this embodiment if event module 36 determines that sensor 14 is not properly installed, system 10 may alert subject 12 that installation is improper (e.g., via user interface 18), flag information related to the output signals generated by sensor 14 while installation is not proper, cease or pause the storage of information to storage module 22 on the portable device until sensor 14 is properly installed on subject 12, record the occurrence of the event (e.g., via a time/date stamp), and/or take other actions in response to the event. In some instances, event module 36 not only detects complete removal of sensor 14, but also improper installation of sensor 14 (e.g., a loose fit between sensor 14 and subject 12), which triggers appropriate action (e.g., any of the above-mentioned courses of action).

In one embodiment, event module 36 detects events related to the other events related to the functionality of system 10. For example, event module 36 may determine events corresponding to battery capacity (e.g., low battery), memory capacity (e.g., full memory), and/or other events related to the functionality of system 10.

In one embodiment, event module 36 detects events related to ambient conditions experienced by subject 12, and/or physiological function of subject 12. For example, these events may include the beginning and/or end of an activity such as exercise, meditation, a nap, and/or other activities.

In one embodiment, event module 36 enables subject 12 to "score" events. The score entered by subject 12 (e.g., via user interface 18) provides an indication of the emotional state of mind, physical pain level, fatigue, and/or other subjective aspects of subject 12's state of being at the occurrence of an event.

Correction module 38 is configured to apply a correction to information related to the one or more output signals generated by sensor 14. In one embodiment, the correction is applied to information determined from the output signal(s) generated by illumination sensor 30. As is discussed further below with respect to FIGS. 8 and 9, in one embodiment, the correction corrects for overlap between the wavelength transfer functions of photodiodes implemented in illumination sensor 30. Other corrections to information determined based on output signals generated by illumination sensor 30, motion sensor 28, proximity sensor 32, and/or other sensors included in sensor 14 can also be determined and/or applied by correction module 38.

Sleep module 40 is configured to determine information related to the sleep of subject 12. This may include sleep cycle information, sleep stage information, wakefulness information, and/or activity information. Sleep module 40 determines such information based on the output signal(s) generated by motion sensor 28. In the embodiment in which system 10 includes a portable device that includes sensor 14, sleep module 40 may be executed by the second processor, to which information is downloaded from the portable device, and/or may be executed on by the first processor on the portable device. Implementation of sleep module 40 solely on the second processor may reduce the storage and/or processing requirements of the portable device, thereby enabling a smaller device with a more appealing form factor. However, inclusion of sleep module 40 on the portable device by the first processor would enable information determined by sleep module 40 to be provided directly to subject 12 via user interface 18 provided on the portable device.

Photon flux module 42 is configured to determine information related to the flux of photons experienced by subject 12 due to ambient illumination. Photon flux module 42 determines this information based on the output signal(s) generated by illumination sensor 30. Flux is determined by dividing the irradiance by the energy per photon, or $\Phi=E/Q/$photon, where $\Phi$ represents flux, E represents the irradiance, and Q/photon represents the energy per photon. It should be appreciated that the energy per photon is wavelength dependent. In order to determine flux in a given portion of the spectrum, some sort of approximation for this energy must be used (since measurement of irradiance for each discrete wavelength across the given portion of the spectrum would be impractical). This approximation is the mean energy per photon within the given portion of the spectrum, and can be calculated as follows:

$$Q_{mean} = \frac{\int_{\lambda_1}^{\lambda_2} Q(\lambda)d\lambda}{\int_{\lambda_1}^{\lambda_2} \lambda d\lambda} \qquad (1)$$

where $Q_{mean}$ represents the mean energy per photon, $Q(\lambda)$ represents the energy as a function of wavelength, $\lambda$ represents the wavelength, and $\lambda_1$ and $\lambda_2$ represent the boundaries of the portion of the spectrum being analyzed. The determined mean energy per photon may then be substituted in the equation above for determining flux as the energy per photon.

Clearly, as the portion of the spectrum being analyzed using the above approximation becomes larger, the larger the inaccuracies inherent in the use of an approximation become. Since illumination sensor 30 provides information related to the intensity (or irradiance) of two or more wavelength ranges, and in one embodiment three wavelength ranges, the determination of overall flux based on the measurements of illumination provided by illumination sensor 30 is enhanced in comparison with determinations based on a single sensor that provides information related to irradiance for the entire visible spectrum. Further, the availability of information related to the intensity and/or irradiance of illumination within the wavelength ranges monitored by illumination sensor 30 enables determinations by photon flux module 42 of the flux within each of the individual wavelength ranges (e.g., using the equations, relationships, and approximations shown above).

Illumination score module 44 is configured to determine a score that represents the resetting effect of the ambient illumination experienced by subject 12 on the circadian phase of subject 12. In one embodiment, determining the score includes determining a weighted sum of the photon fluxes of illumination in the two or more wavelength ranges monitored by illumination sensor 30 (as determined by photon flux module 42. For instance, in the embodiment in which illumination sensor 30 monitors one wavelength range that corresponds to the red portion of the visible spectrum, another wavelength range that corresponds to the green portion of the visible spectrum, and another wavelength range that corresponds to the blue portion of the visible spectrum, the weighted sum is a sum of the photon fluxes of each of these wavelength ranges multiplied by corresponding weighting coefficient. This may be represented mathematically as:

$$S = \Phi_{red} * \phi_{red} + \Phi_{green} * \phi_{green} + \Phi_{blue} * \phi_{blue};$$

where $\Phi_{red}$, $\Phi_{green}$, and $\Phi_{blue}$ represent the photon fluxes in the red, green, and blue portions of the visible spectrum, respectively, $\phi_{red}$, $\phi_{green}$, and $\phi_{blue}$ represent the weighting factors for the red, green, and blue portions of the visible spectrum respectively, and S represents the score of the ambient illumination. The relative magnitude of $\phi_{red}$, $\phi_{green}$, and $\phi_{blue}$ reflect the relative impact of ambient illumination in the red, green, and blue portions of the visible spectrum in resetting the circadian phase of subject 12.

In one embodiment, the weighting factors $\phi_{red}$, $\phi_{green}$, and $\phi_{blue}$, further reflect the variance of the relative impact of ambient illumination within the various portions of the visible spectrum with the intensity of ambient illumination. For example, at relatively low intensities, the circadian phase resetting impact of illumination within the blue portion of the visible spectrum may be at a maximum. As the relative intensity of the ambient illumination increases, the relative impact of illumination within the blue portion of the spectrum may decrease with respect to the resetting impact of illumination within the green portion of the spectrum. In order to account for this variation with intensity, in one embodiment, illumination score module 44 determines the weighting factors $\phi_{red}$, $\phi_{green}$, and $\phi_{blue}$ as a function of the intensity of ambient illumination (as determined based on the output signal(s) generated by illumination sensor 30).

Figure 2:
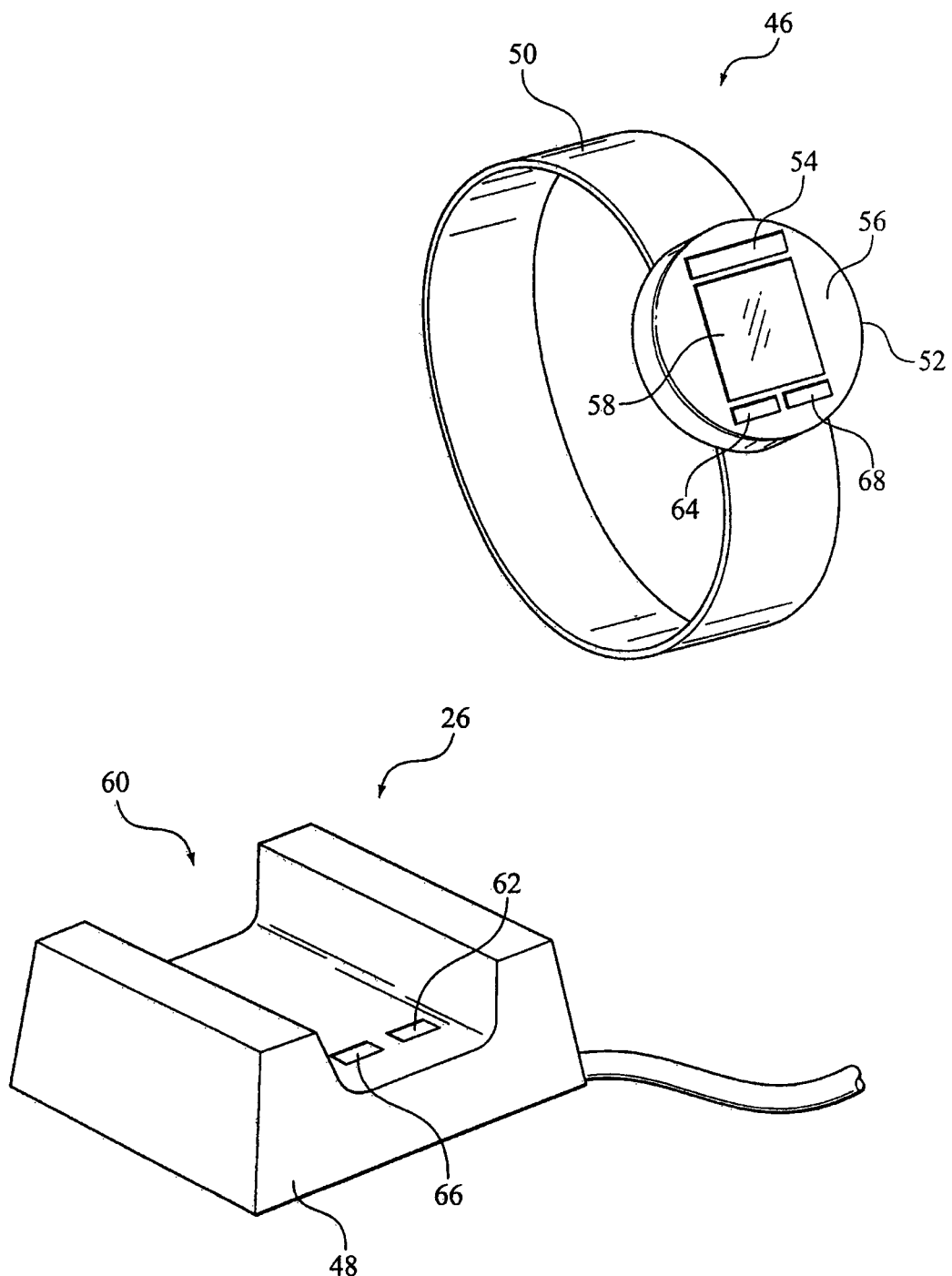
FIG. 2 illustrates components of a system configured to determine information related to the context and/or physiological function of a subject, according to one embodiment of the invention.

FIG. 2 illustrates an embodiment of system 10 including a portable device 46 and a docking device 48. Portable device 46 illustrated in FIG. 2 is one embodiment of the portable device discussed above including a first processor (not shown in FIG. 2) disposed within a portable device (e.g., portable device 46), and a second processor that receives information from the first processor and/or a storage module (not shown in FIG. 2) disposed within the portable device for further processing and/or storage. In the embodiment illustrated in FIG. 2, portable device 46 includes a strap 50 configured to be engaged with an appendage of subject 12 so that portable device 46 is wearable by subject 12. For example, portable device 46 may be worn on the wrist of subject 12 similarly to a conventional wristwatch. It should be appreciated, however, that the particular design of portable device 46 described hereafter is not intended to be limiting, and that other portable devices may be implemented. For instance, a portable personal electronic device other than a wristwatch (e.g., a personal digital assistant, a mobile telephone, a handheld computer, etc.) may be implemented to provide some or all of the functionality discussed herein with respect to portable device 46 (e.g., for monitoring ambient illumination).

In the embodiment of portable device 46 illustrated in FIG. 2, a housing 52 of device 46 houses the first processor, the storage module, and sensor 14 (not shown in FIG. 2). In particular, illumination sensor 30 (not shown in FIG. 2) may be accessible to ambient illumination via an optically transparent window 54 formed on a face 56 of housing 52. As subject 12 wears portable device 46, illumination sensor 30 receives the ambient light experienced by subject 12 via window 54, and generates one or more output signals in response thereto, as described above.

In one embodiment, sensor 14 disposed within housing 52 further comprises motion sensor 28 (not shown in FIG. 2). As was discussed above, motion sensor 28 generates one or more output signals that convey information related to the position and/or motion of motion sensor 28, which corresponds to the body motion of subject 12, since device 46 is worn by subject 12.

In one embodiment, sensor 14 comprises proximity sensor 32 (not shown in FIG. 2) disposed within housing 52 and/or strap 50. As was discussed above, proximity sensor 32 generates one or more output signals that convey information related to the installation of sensor 14 and portable device 46 on subject 12. This information may be implemented in the storage and/or processing of the information related to the body motion of subject 12 and/or the ambient illumination experienced by subject 12 during use of portable device 46.

As can be seen in FIG. 2, portable device 46 includes a display screen 58 disposed on face 56 of housing 52. In one embodiment, display 58 includes a Liquid Crystal Display ("LCD") that displays information to subject 12. Display 58 forms at least a part of user interface 18 described above with respect to FIG. 1. As such, display 58 may convey information to subject 12 regarding her physiological function, her context, and/or the proper or improper function of device 46. For example, display 58 may provide a time display that displays to subject 12 the time of day. Display 58 may further include an indicator that indicates to subject 12 that device 46 is properly installed and functioning normally. In one embodiment, when a predetermined monitoring period, during which device 46 is to be used to monitor the context and/or physiological function of subject 12, has expired, display 58 may convey this to subject 12. For example, the time of day display may go blank, thereby indicating to subject 12 that the monitoring period is over. In other embodiments, this indication may include another visual indicator and/or an audible alarm sounded by device 46.

In one embodiment, timer 16 (not shown in FIG. 2) is included within housing 52, and the first processor disposed within device 46 comprises compression module 34. As output signals are generated by sensor 14, information derived from the output signals is compressed (e.g., as described above) and stored to the storage module included within housing 52 for later retrieval and processing. This embodiment is not intended to be limiting, as it should be understood from the foregoing description of both FIGS. 1 and 2 that the first processor included in device 46 may further include one or more of modules 36, 38, 40, 42, and/or 44 as described above with respect to FIG. 1. Further, it should be appreciated that in an embodiment including one or more of these additional modules, the information generated by the additional module(s) may be conveyed directly to subject 12 via display 58 without having to be further processed remotely from device 46.

Docking device 48 is configured to receive portable device 46 at a docking section 60. Docking device 48 may form a portion of communication system 26 discussed briefly above with respect to FIG. 1, in that docking station 48 is coupled to a host processing system (e.g., a personal computer) and includes a communication interface 62 at the docking section 60 configured to interface with a corresponding communication interface 64 formed on device 46 that enables communication between the first processor and/or the storage module included within housing 52 of device 46 and the host processing system with which docking device 48 is coupled. Information is communicated back and forth between the processor and/or storage of device 46 and the host processing system such that host processing system retrieves information from device 46, and further processes the information. For example, one or more of modules 36, 38, 40, 42, and/or 44 as described above with respect to FIG. 1 may be formed by the host processing system, and the user interface of the host processing system may enable a user (e.g., subject 12, a caregiver, etc.) to access the information retrieved from device 46 and/or the information generated by any of modules 36, 38, 40, 42, and/or 44 formed on the host processing system.

In one embodiment, communication interfaces 62 and 64 enable optical infrared signals to be implemented to transmit information back and forth between docking device 48 and portable device 46. However, this is not intended to be limiting. For example, in one embodiment, communication interfaces 62 and 64 include one or more of electrical contacts for hardwired transmission. In another embodiment, the "interface" between docking device 48 and portable device 46 may be wireless (e.g., by radio frequency transmission), and proximity would not be requisite for the transmission of information therebetween.

Docking device 48, as shown in FIG. 2 further includes a power interface 66 that operates to interface with a corresponding power interface 68 formed on housing 52. Via power interfaces 66 and 68, power may be provided to portable device 46 to recharge power module 20 (not shown in FIG. 2) disposed within device 46 while device 46 is docked to docking device 48.

Figure 3:
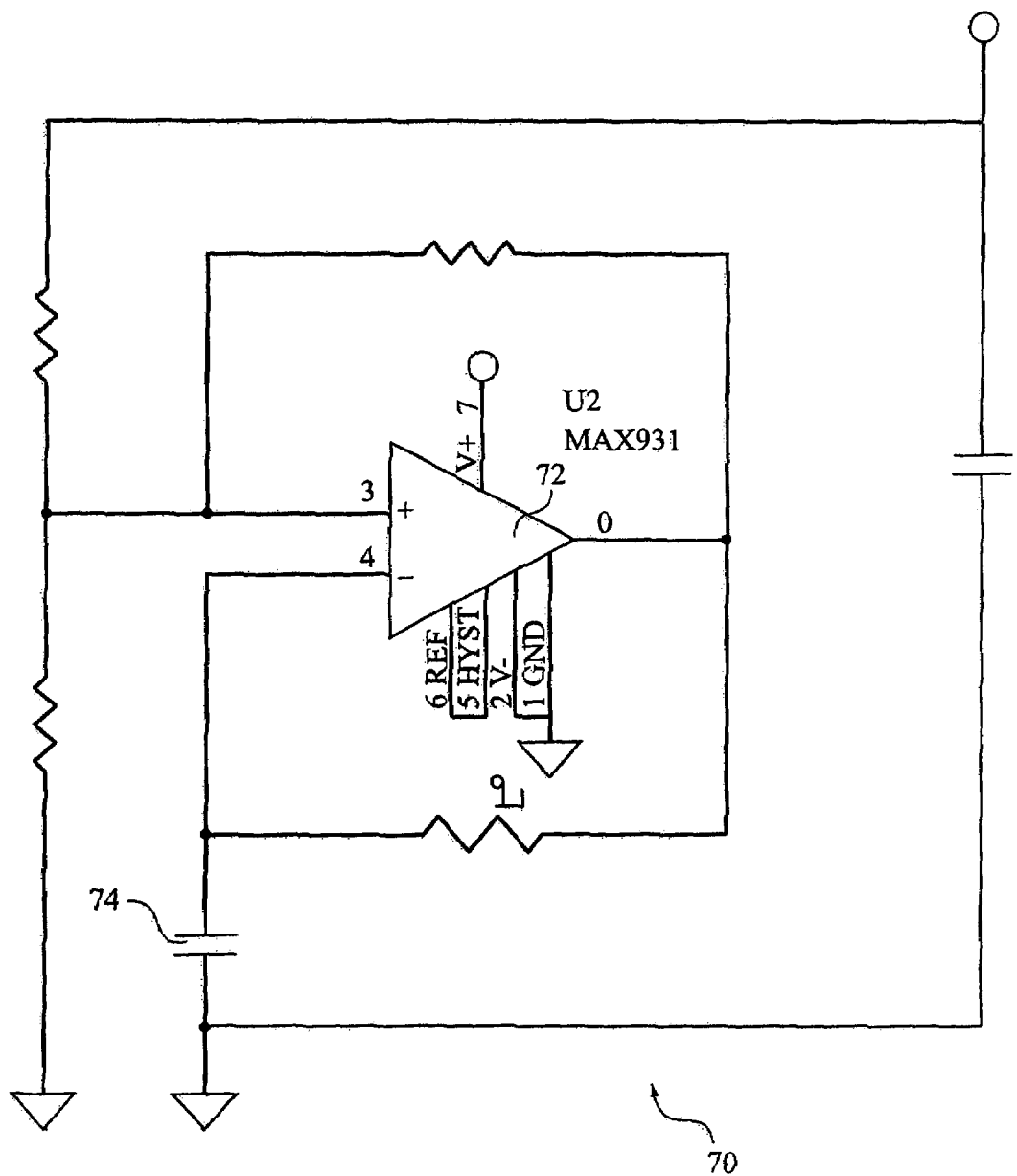
FIG. 3 illustrates a proximity sensor, in accordance with one embodiment of the invention.

FIG. 3 illustrates a circuit diagram of one embodiment of proximity sensor 32 of sensor 14. In the embodiment shown, proximity sensor 32 includes a capacitive sensor multivibrator 70, a comparator 72 (which may be formed as a module within the second processor or as a separate processing unit), and two contacts that collectively form a capacitor 74. The two contacts are conductive (e.g., metallic), but do not have to necessarily be placed in contact with the skin of subject 12 to enable sensor 32 to function. For example, the contacts may be formed by metallic elements disposed within housing 52 and/or strap 50 of portable device 46 illustrated in FIG. 2.

Returning to FIG. 3, if the output of comparator 72 is high, capacitor 74 charges. If the voltage at the negative terminal of comparator 72 exceeds the voltage at the positive terminal, the output of comparator 72 goes low and capacitor 74 discharges. This, in turn, again causes the voltage at the negative terminal of comparator 72 to drop below the voltage on the positive terminal, which makes the output of comparator 72 to go high again, allowing capacitor 74 to recharge. The frequency of this oscillation is determined, in part, by capacitance of capacitor 74 formed by the contacts. Since the capacitance of capacitor 74 changes between air and close proximity to the skin of subject 12, the frequency of the oscillation described above to change in a predictable relationship with the proximity of the contacts of capacitor 74 to subject 12, thereby enabling a determination of the proximity of subject 12 to sensor 32. This detection of proximity enables a determination of the effectiveness of the installation of sensor 32 (and with it the other sensors 28 and/or 30 of sensor 14) on subject 12.

Figure 4:
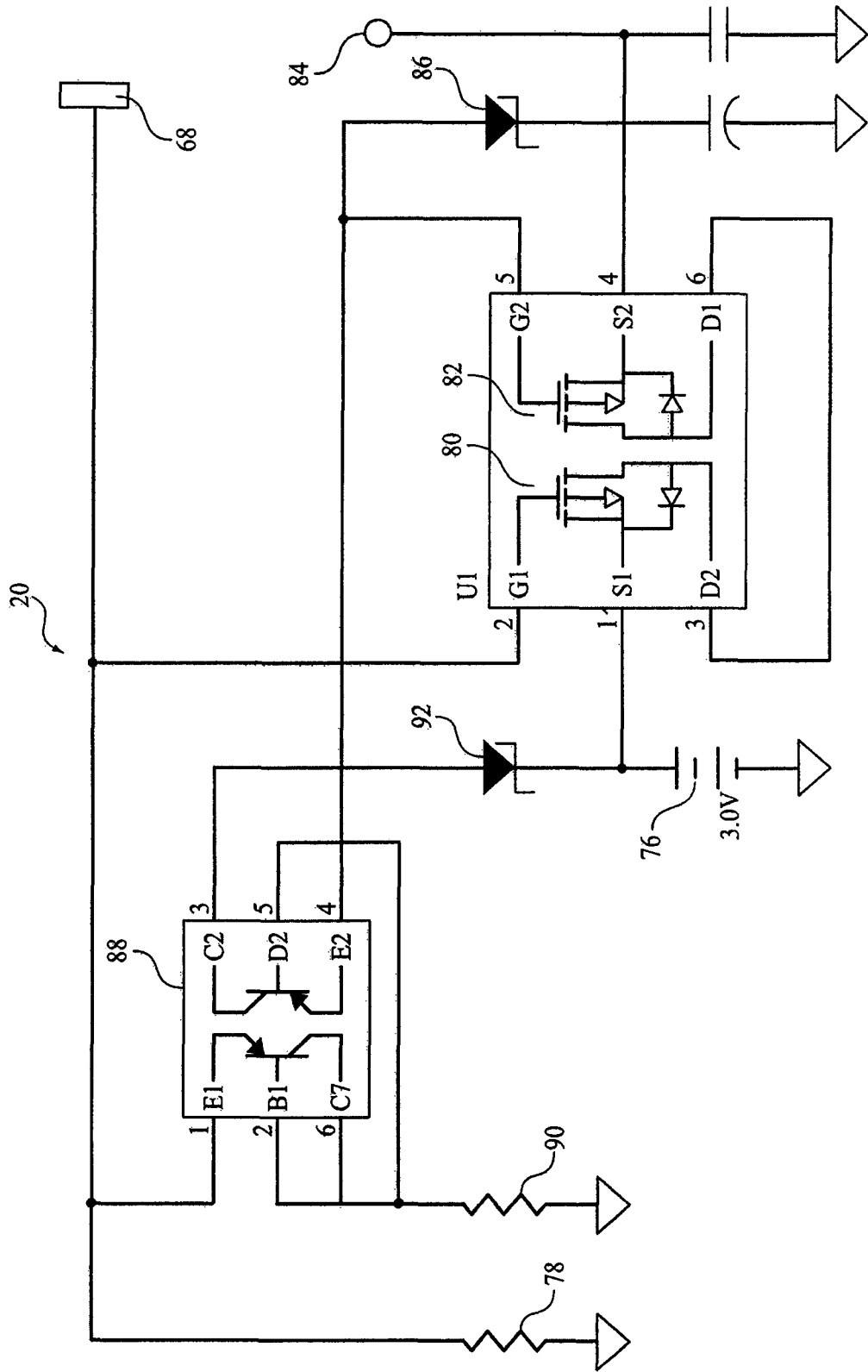
FIG. 4 illustrates a power module, in accordance with one embodiment of the invention.

FIG. 4 illustrates a circuit diagram of a battery charging circuit that is included in one embodiment of power module 20 to recharge a battery 76 power module 20. External power may be applied to the circuit at power interface 68. When no external power is applied to power interface 68, a resistor 78 forces gates of two FET switches 80 and 82 included in the circuit low. In this condition, switches 80 and 82 are turned on, allowing battery 76 to provide power to an output 84 of power module 20. A first diode 86 blocks leakage current from running back through power interface 68 to ground. When an external power supply is applied to power interface 68, switches 80 and 82 are turned off, thus disconnecting battery 76 from output 84. Power is provided to output 84 from power interface 68 through diode 86. This allows power module 20 to power components of system 10, even if the battery voltage of battery 76 is below a circuit minimum. While power is applied to power interface 68, a current regulator 88 become a current source with the current set by the voltage applied at power interface 68 and a resister 90. This current source then recharges battery 76 through a diode 92. Since current regulator 88 and diode 92 contribute voltage drops, the current is only constant until battery voltage reaches a predetermined threshold, after which, as the battery voltage increases, the charging current decreases. This reduces battery charging time compared to a simple constant voltage charging circuit.

Figure 5:
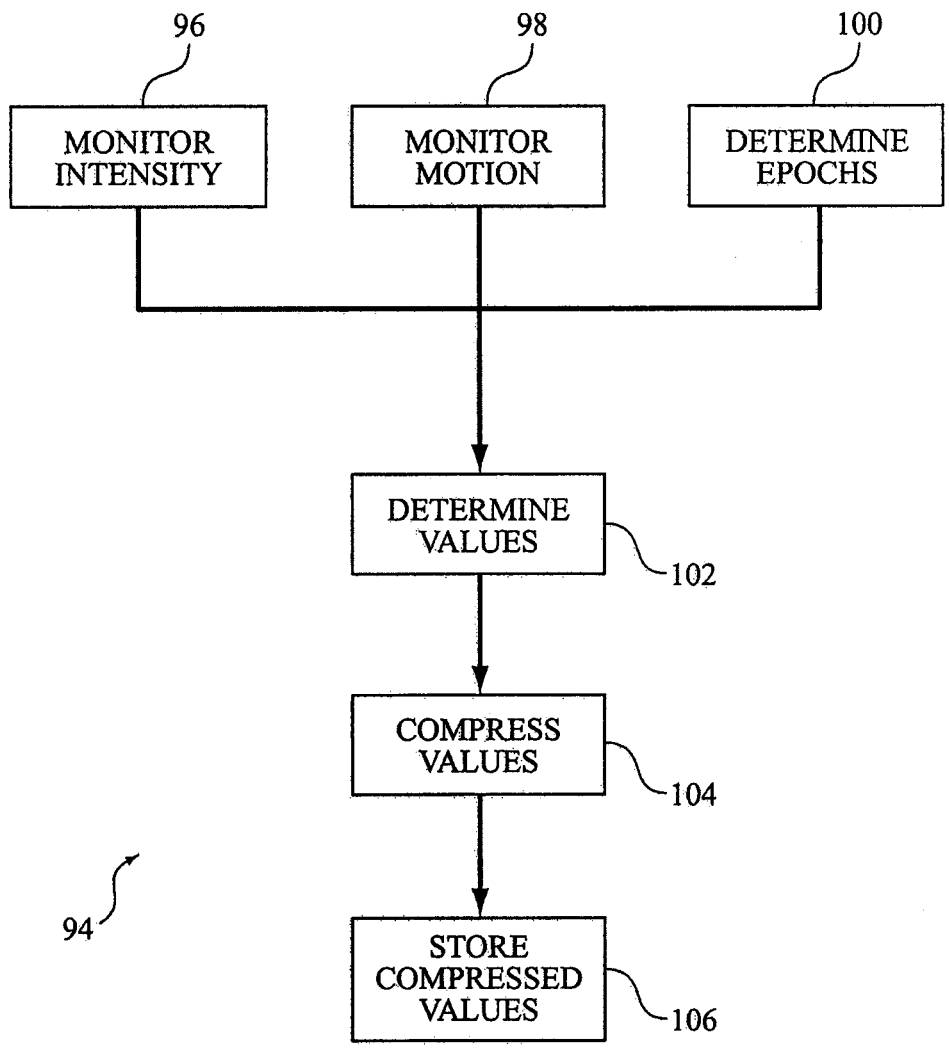
FIG. 5 illustrates a method of monitoring ambient illumination experienced by a user, according to one embodiment of the invention.

FIG. 5 illustrates a method 94 of monitoring ambient illumination experienced by a subject. Although the operations of method 94 are discussed below with respect to the components of system 10 described above and illustrated in FIGS. 1-4, it should be appreciated that this is for illustrative purposes only, and that method 94 may be implemented with alternative components and/or systems without departing from the scope of this disclosure.

In one embodiment, method 94 comprises an operation 96 at which an intensity of ambient illumination is monitored in two or more separate wavelength ranges. The two or more separate wavelength ranges may include three wavelength ranges. The two or more separate wavelength ranges may include a first wavelength range corresponding to the red portion of the visible spectrum, a second wavelength range, corresponding to the green portion of the visible spectrum, and a third wavelength range corresponding to the blue portion of the visible spectrum. In some instances, operation 96 may be executed by an illumination sensor similar to illumination sensor 30, described above and illustrated in FIGS. 1 and 2.

At an operation 98 motion of the subject is monitored. In one embodiment, operation 98 is performed by a motion sensor similar to motion sensor 28, described above and illustrated in FIG. 1.

At an operation 100, the passage of individual periods of time is determined. In one embodiment, operation 100 is executed by a timer similar to timer 16, described above and illustrated in FIG. 1.

At an operation 102, values representing information related to the ambient illumination experienced by the subject during individual periods of time and/or values representing information related to the motion of the subject during the individual periods of time are determined. The values are determined based on information related to the ambient illumination experienced by the subject determined at operation 96, information related to the motion of the subject determined at operation 98, and/or the passage of periods determined at operation 100. In one embodiment, operation 102 is executed by a processor similar to processor 24 described above and shown in FIG. 1.

At an operation 104, values determined at operation 102 are compressed for storage. In one embodiment, receives the values representing information related to ambient illumination and/or motion of the subject for individual periods of time, and compresses the representations by expressing a series of periods (i) that are proximate to each other in time, and (ii) for which the representations of the output signal have a similar value, as (a) a value representative of the representations of the output signal for the periods included in the series and (b) the number of periods included in the series of periods. Operation 104 may be executed by a compression module similar to compression module 34 shown in FIG. 1 and described above.

At an operation 106, the information compressed at operation 104 is stored. In one embodiment, the information stored at operation 104 is stored in a storage module similar to storage module 22 described above and illustrated in FIG. 1.

Figure 6:
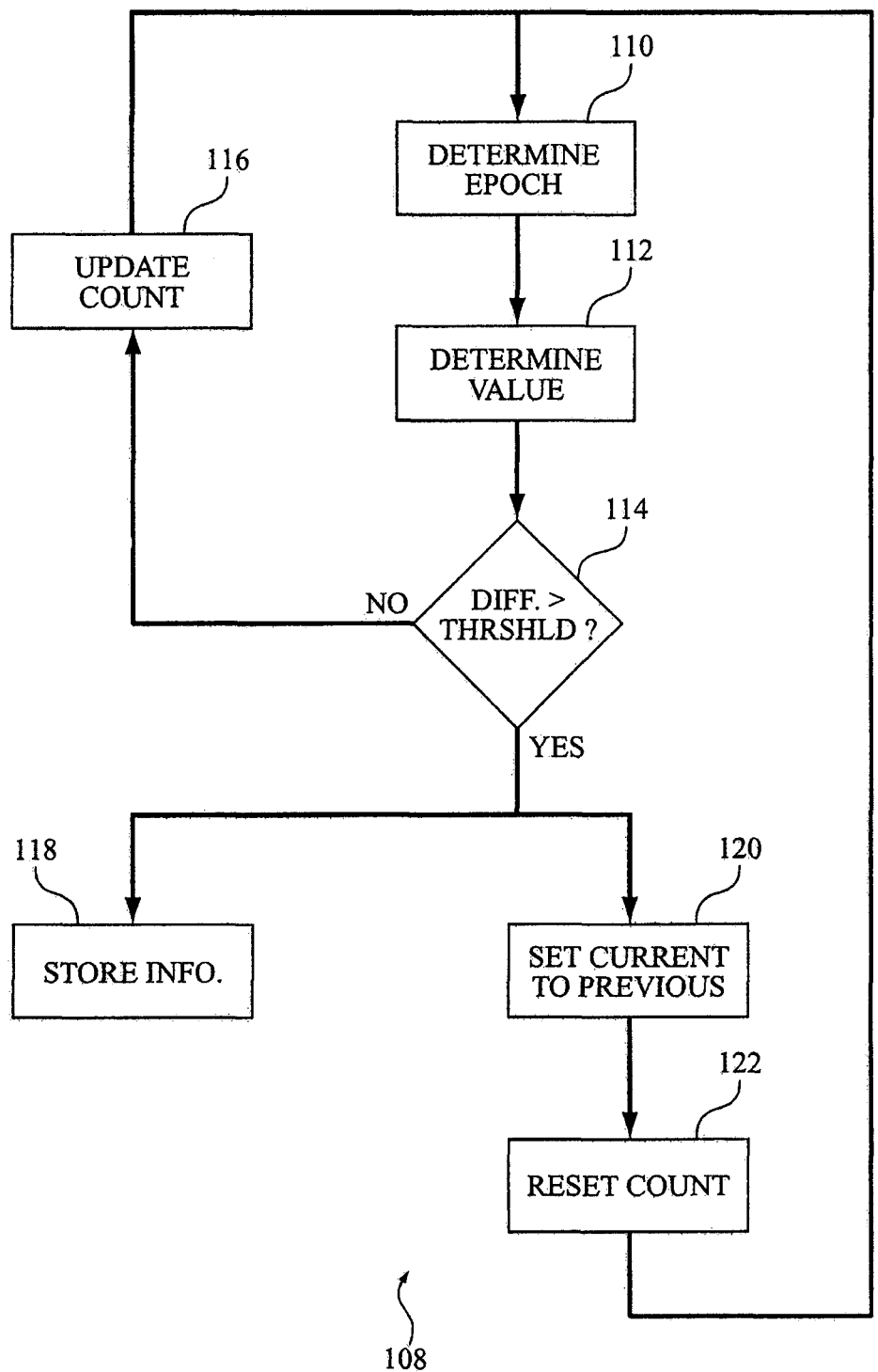
FIG. 6 illustrates a method of compressing information related to the context and/or the physiological function of a user, according to one embodiment of the invention.

FIG. 6 illustrates a method 108 of compressing information related to the context and/or the physiological function of a subject. In one embodiment, method 108 is implemented as operation 104 within method 94, described above and shown in FIG. 5. However, this is not intended to be limiting, as method 108 can be implemented within a variety of contexts.

At an operation 110, a passage of a current period in time is determined. At an operation 112, a value of a parameter related to the context and/or the physiological function of the subject is determined for the current period in time. For example, the parameter may include a parameter related to the intensity of ambient illumination, body motion of the subject, and/or other contextual or physiological information.

At an operation 114 a determination is made as to whether a difference between the value of the parameter for the current period in time and the value of the parameter for a previous period in time exceeds a predetermined threshold. In some instances, the predetermined threshold may require substantial equivalence between the two values. In other instances, a larger threshold is employed to enable some variation between the value for the current period and the value for the previous period.

If the difference between the values does not exceed the predetermined threshold, then method 108 proceeds to operation 116 where a count of periods for which the difference between the values has not exceeded the predetermined threshold is increased by 1, and control returns to operations 110 and 112.

If the difference between the values exceeds the predetermined threshold, then method 108 proceeds to operations 118 and 120. At operation 118, the value of the parameter for the previous period is stored with the current count (as kept, e.g., by operation 116). If method 108 is being implemented within method 94 (shown in FIG. 5) as operation 104, operation 118 is implemented as operation 106 of method 94. Returning to method 108, at operation 120, the value of the current period is saved as the value of the previous period for comparison with subsequent periods, and method 108 proceeds to operation 122. At operation 122, the count (e.g., as kept by operation 116 and stored at operation 118) is reset to zero. From operation 122, method 108 proceeds back to operations 110 and 112.

Figure 7:
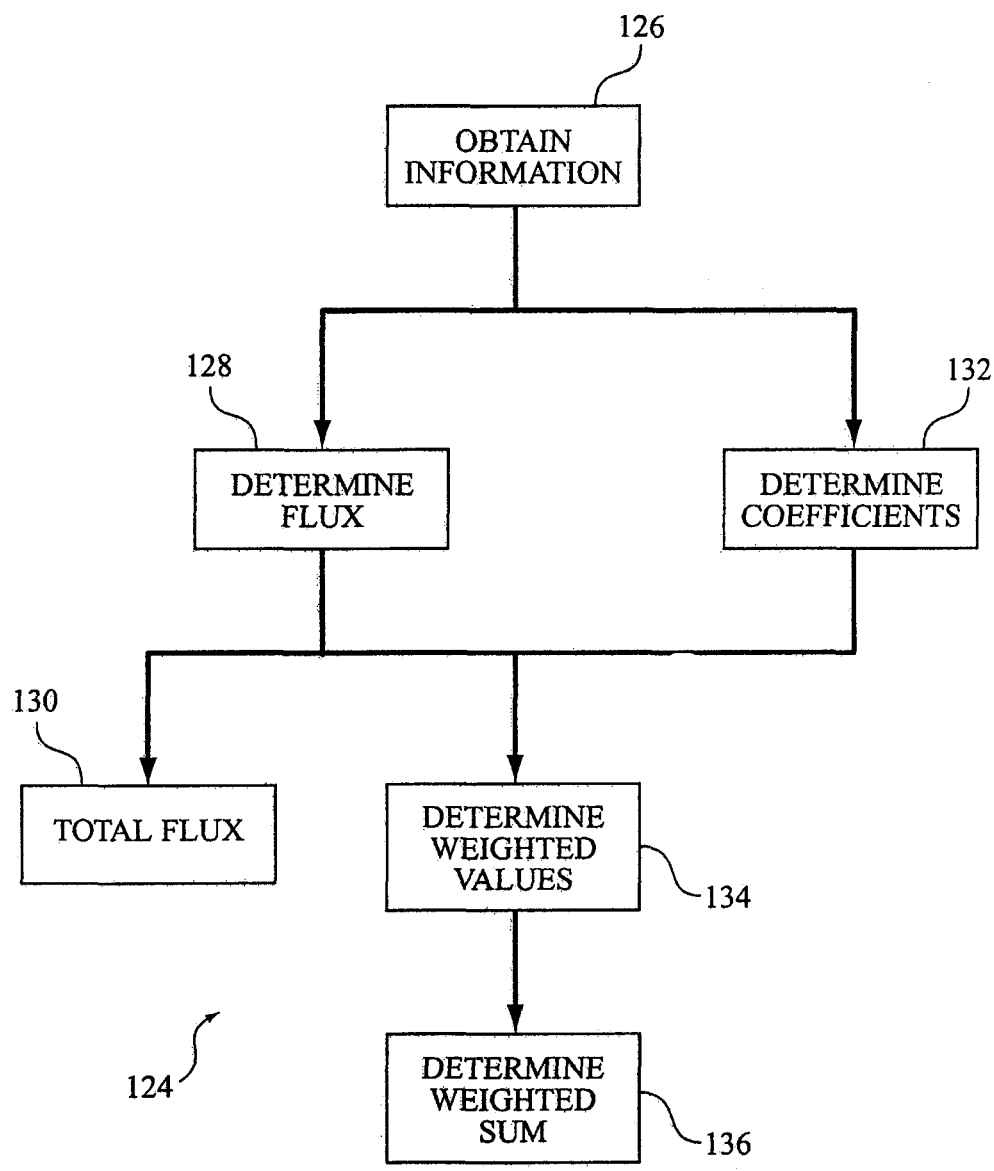
FIG. 7 illustrates a method of determining a score that represents the resetting effect of ambient illumination on the circadian phase of a user, in accordance with one embodiment of the invention.

FIG. 7 illustrates a method 124 of determining a score that represents the resetting effect of ambient illumination on the circadian phase of a subject. In one embodiment, method 124 is implemented by illumination score module 44, described above and illustrated in FIG. 1. However, other implementations of method 124 are contemplated.

Method 124 includes an operation 126 at which information related to the intensity of ambient illumination is obtained. This information may include the intensities of individual wavelength ranges of ambient illumination and/or an overall intensity of ambient illumination. In one embodiment, operation 126 comprises retrieving stored information related to the intensity of ambient illumination. In another embodiment, operation 126 comprises obtaining the information directly from one or more illuminations sensors.

At an operation 128, information related to the photon flux of ambient illumination within two or more wavelength ranges is determined based on the information obtained at operation 126. In one embodiment, the total photon flux of ambient illumination is determined at an operation 130 based on the information determined at operation 126.

At an operation 132, weighting coefficients are determined for each of the two or more wavelength ranges. In one embodiment, determining the weighting coefficients comprises accessing stored constant values. In another embodiment, determining the weighting coefficients comprises determining the weighting coefficients as a function of the information obtained at operation 126. At an operation 134, the weighting coefficients for the two or more wavelength ranges are multiplied by the photon fluxes of the two or more wavelength ranges determined at operation 128. This multiplication yields a weighted value for each of the two or more wavelength ranges.

At an operation 136, the score of the ambient illumination is determined by summing the weighted values determined at operation 134.

Figure 8:
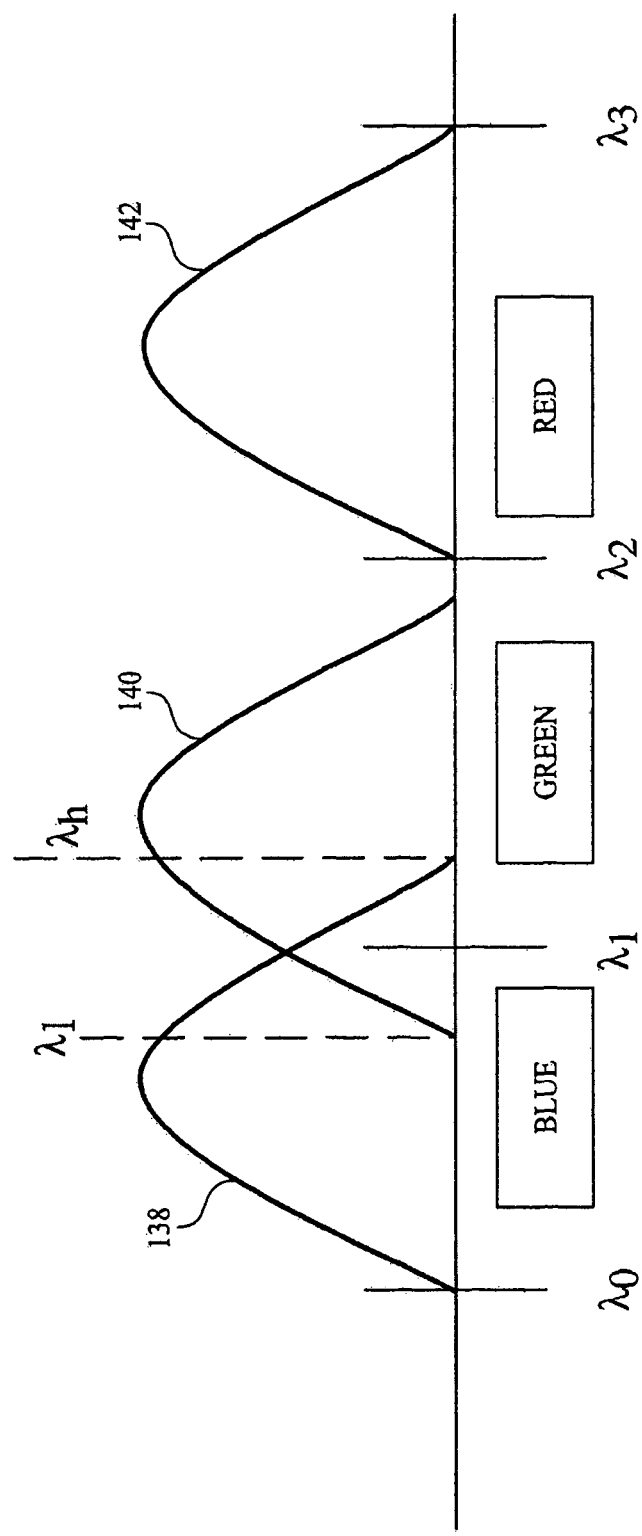
FIG. 8 illustrates a set of wavelength response functions, in accordance with one embodiment of the invention.

As has been discussed above, one of the features of this disclosure is the monitoring of ambient illumination within two or more wavelength ranges. In one embodiment, this includes employing a plurality of photodiodes (either formed individually or as an integrated array) where one or more of the photodiodes corresponds to on of the two or more wavelength ranges to be monitored. In practice, this typically involves implementing photodiodes where the wavelength response functions of the different photodiodes have some spectral overlap. For example, this principle is illustrated in FIG. 8, which shows sample wavelength response functions 138, 140, and 142 (wavelength vs. conversion factor) that correspond to photodiodes that monitor ambient illumination within the blue, green, and red portions of the visible spectrum, respectively. It should be appreciated that this depiction of the wavelength response functions is provided for illustrative purposes only, and that actually wavelength response functions may not have such regular shape, and/or may include a greater amount of "spreading" at the bases of the functions. Further, the use of the specific spectral sections shown (e.g., blue, green, and red) is not intended to be limiting, as other combinations of photodiodes that monitor illumination within different spectral regions (e.g., cyan, magenta, and yellow) are contemplated.

As can be seen in FIG. 8, although the "blue" portion of the spectrum extends from $\lambda_\delta$ to $\lambda_1$, the wavelength responses 138 and 140 of the photodiodes do not coincide exactly with these boundaries. Instead, the wavelength responses 138 and 140 of the blue photodiode and the green photodiode overlap such that a portion of the wavelength response function 138 of the blue photodiode crosses into the "green" portion of the spectrum (e.g., $>\lambda_1$), and a portion of the wavelength response function 140 of the green photodiode crosses into the "blue" portion of the spectrum (e.g., $<\lambda_1$). If this overlap is not corrected for, illumination in the green portion of the spectrum will be attributed by the blue photodiode to the blue portion of the spectrum and illumination in the blue portion of the spectrum will be attributed to the green portion of the spectrum as it is detected by the green photodiode.

This example of wavelength response overlap is not limited to instances in which a photodiode corresponding to the blue portion of the spectrum and a photodiode corresponding to the green portion of the spectrum are implemented. In the majority of instances in which photodiodes are implemented that correspond to proximate sections of the spectrum, such an overlap is probable. However, the overlap may be more or less exacerbated depending on the relative proximity between the portions of the spectrum and the actual response functions of the photodiodes. For example, in practice, there is typically some overlap between the response function of the red photodiode and the green photodiode. This overlap tends to be less than the overlap between the blue and green photodiodes and, thus, may be ignored in one embodiment, or may be corrected for as described hereafter for the blue and the green photodiodes.

Figure 9:
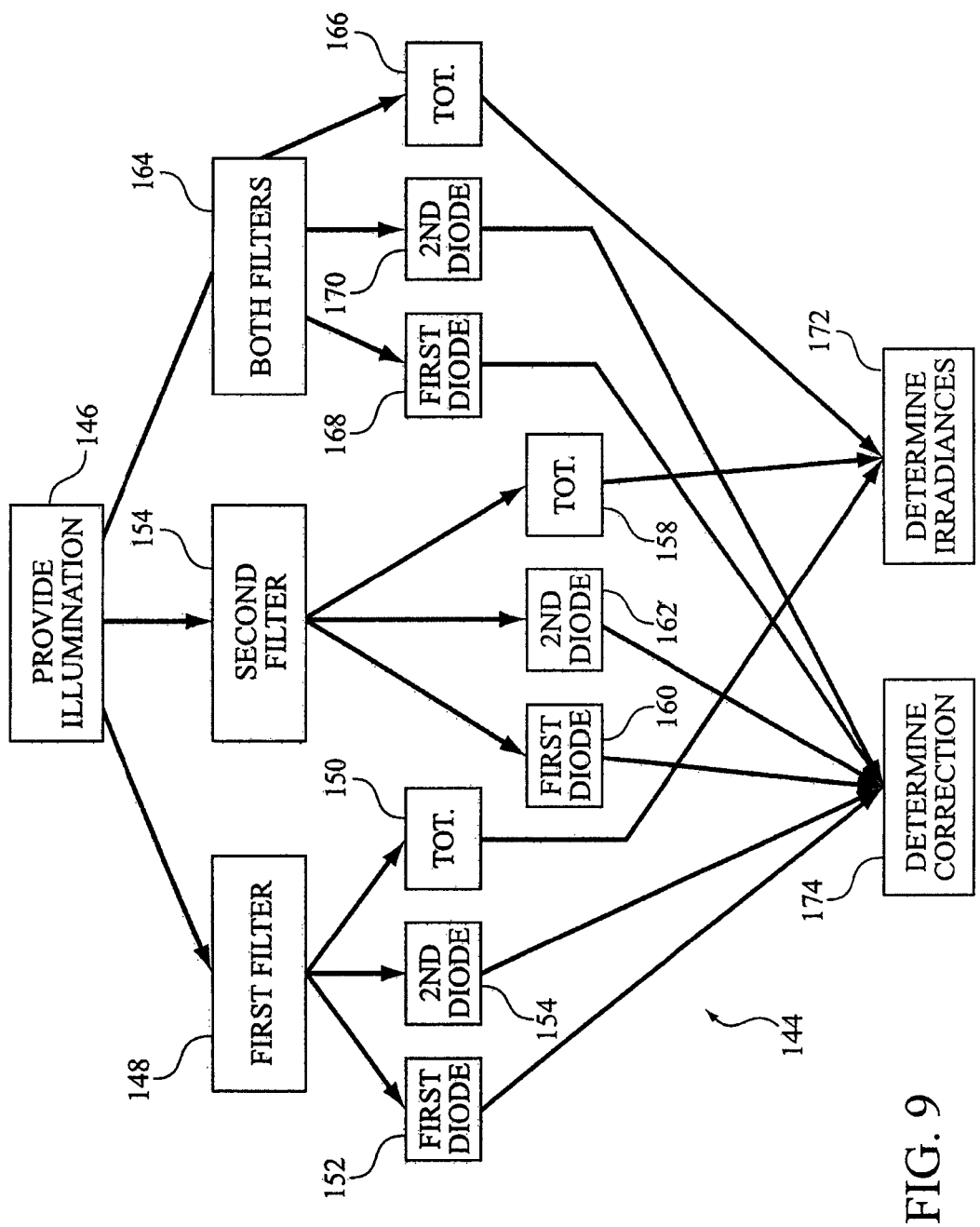
FIG. 9 illustrates a method of determining a correction for an overlap of wavelength response functions in illumination sensors, according to one embodiment of the invention.

FIG. 9 illustrates a method 144 of determining a correction that reduces the imprecision of the implementation of the photodiodes corresponding to wavelength response functions 138 and 140 (or any other overlapping response functions). At an operation 146, radiation is provided. The provided radiation has a smoothly varying wavelength over the overlapping wavelength response functions. For example, operation 146 can be performed by a blackbody radiation source that provides blackbody radiation.

At an operation 148, a first filter having a transmission function that corresponds substantially to a first one of the wavelength response functions (e.g., wavelength response function 138 shown in FIG. 8) is used to filter the provided radiation. In one embodiment, the correspondence between the transmission function of the first filter and the first one of the wavelength response functions comprises approximate equality between the cut-ins and cut-outs of the transmission and wavelength response functions. In one embodiment, the correspondence between the transmission function of the first filter and the first one of the wavelength response functions comprises an approximate equality between the peaks of the transmission and wavelength response functions. In one embodiment, the correspondence between the transmission function of the first filter and the first one of the wavelength response functions comprises both of the transmission and wavelength response functions being located in a corresponding portion of the spectrum (e.g., the blue portion of the spectrum).

Method 144 further includes a set of operations 150, 152, and 154 wherein a set of measurements of the filtered illumination created at operation 148 are taken. These measurements may be taken serially, or in parallel. At operation 150, a measurement of the total irradiance of the filtered illumination is taken via an illumination sensor that is not wavelength specific (e.g., a photometer). At operation 152, an output signal (e.g., the output current) of the blue photodiode is determined while the blue photodiode is exposed to the filtered illumination created at operation 148. At operation 154, an output signal (e.g., the output current) of the green photodiode is determined while the green photodiode is exposed to the filtered illumination.

At an operation 156, the radiation provided at operation 146 a second filter having a transmission function that corresponds substantially to a second one of the wavelength response functions (e.g., wavelength response function 140 shown in FIG. 8) is used to filter the provided radiation. In one embodiment, the correspondence between the transmission function of the second filter and the second one of the wavelength response functions comprises approximate equality between the cut-ins and cut-outs of the transmission and wavelength response functions. In one embodiment, the correspondence between the transmission function of the second filter and the second one of the wavelength response functions comprises an approximate equality between the peaks of the transmission and wavelength response functions. In one embodiment, the correspondence between the transmission function of the second filter and the second one of the wavelength response functions comprises both of the transmission and wavelength response functions being located in a corresponding portion of the spectrum (e.g., the green portion of the spectrum).

At a set of operations 158, 160, and 162 a set of measurements of the filtered illumination created at operation 156 are taken. These measurements may be taken serially, or in parallel. At operation 158, a measurement of the total irradiance of the filtered illumination is taken via the illumination sensor that is not wavelength specific. At operation 160, an output signal of the blue photodiode is determined while the blue photodiode is exposed to the filtered illumination created at operation 156. At operation 162, an output signal of the green photodiode is determined while the green photodiode is exposed to the filtered illumination.

At an operation 164, the illumination provided at operation 146 is filtered with both of the first and the second filter. A set of measurements of the filtered illumination created at operation 164 are then taken at operations 166, 168, and 170. Again, these measurements may be taken serially, or in parallel. At operation 166, a measurement of the total irradiance of the filtered illumination is taken via the non-wavelength specific illumination sensor. At operation 168, an output signal of the blue photodiode is determined while the blue photodiode is exposed to the filtered illumination created at operation 164. At operation 170, an output signal of the green photodiode is determined while the green photodiode is exposed to the filtered illumination.

Returning briefly to FIG. 8, the irradiance detected at operation 150 will include an irradiance caused by illumination from the blue filter in the blue portion of the spectrum (between $\lambda_0$ and $\lambda_1$) ("$\in_{BB}$") and an irradiance caused by illumination from the blue filter in the green portion of the spectrum (between $\lambda_0$ and $\lambda_1$) ("$\in_{BG}$"). Similarly, the irradiance detected at operation 158 will include an irradiance caused by illumination from the green filter in the green portion of the spectrum ("$\in_{GB}$") and an irradiance caused by illumination from the green filter in the blue portion of the spectrum ("$\in_{GB}$"). The irradiance at operation 166 will include irradiance caused essentially by only the portions of the transmission functions of the green and blue filters that overlap between the cut-in of the transmission function of the green filter ("$\lambda_1$") and the cut-out of the transmission function of the blue filter ("$\lambda_h$").

Turning back to FIG. 9, at an operation 172, $\in_{BB}$, $\in_{GG}$, $\in_{BG}$, and $\in_{GB}$ are determined from the measurements made at operations 150, 158, and 166 based on a previously derived relationship between the measurements made at operations 150, 158, and 166 and $\in_{BB}$, $\in_{GG}$ 813, and $\in_{GB}$. One possible process for deriving these relationships follows.

Referring again to FIG. 8, the total irradiance of the illumination filtered with the blue filter ("$E_B$") (e.g., at operation 148 of method 144) can be expressed as:

$$E_B = \varepsilon_{BB} + \varepsilon_{BG} = \frac{1}{(\lambda_1 - \lambda_0)} \int_{\lambda_0}^{\lambda_1} \varepsilon_B(\lambda) d\lambda + \frac{1}{(\lambda_2 - \lambda_1)} \int_{\lambda_1}^{\lambda_2} \varepsilon_B(\lambda) d\lambda; \quad (3)$$

where $\in_B(\lambda)$ represents the irradiance of the illumination filtered by the blue filter as a function of the wavelength. Similarly, the total irradiance of the illumination filtered with the green filter ("$E_G$") (e.g., at operation 156 of method 144) can be expressed as:

$$E_G = \varepsilon_{GB} + \varepsilon_{GG} = \frac{1}{(\lambda_1 - \lambda_0)} \int_{\lambda_0}^{\lambda_1} \varepsilon_G(\lambda) d\lambda + \frac{1}{(\lambda_2 - \lambda_1)} \int_{\lambda_1}^{\lambda_2} \varepsilon_G(\lambda) d\lambda; \quad (4)$$

where $\in_G(\lambda)$ represents the irradiance of the illumination filtered by the green filter as a function of the wavelength.

Assuming that the irradiance function for any region of the spectrum ("$\in(\lambda)$") for a given filter can be expressed as $\in(\lambda) = W(\lambda)F(\lambda)$, where $W(\lambda)$ represents the irradiance of the filtered white light as a function of wavelength and $F(\lambda)$ represents the transmission function of the given filter as a function of wavelength, then the measurement of irradiance obtained at operation 166 of method 144 ("$E_C$") can be expressed as:

$$E_C = \frac{1}{(\lambda_{li} - \lambda_l)} \int_{\lambda_i}^{\lambda_{li}} W(\lambda) F_B(\lambda) F_G(\lambda) d\lambda; \quad (5)$$

where $F_B(\lambda)$. represents the transmission function of the blue filter, and $F_G(\lambda)$. represents the transmission function of the green filter.

By assuming that the illumination being filtered (provided at operation 146 of method 144) is approximately blackbody radiation, that that $F_G(\lambda)$ is constant between $\lambda_1$ and $\lambda_2$, and that $F_G(\lambda)$ and $F_B(\lambda)$ are symmetrical about $\lambda_1$, equation (5) simplifies to:

$$E_C = \frac{2}{(\lambda_{li} - \lambda_1)} \overline{F}_G \int_{\lambda_1}^{\lambda_{li}} W(\lambda) F_B(\lambda) d\lambda = 2\overline{F}_G \frac{1}{(\lambda_{li} - \lambda_1)} \int_{\lambda_1}^{\lambda_{li}} \varepsilon_B(\lambda) d\lambda; \quad (6)$$

where $\overline{F}_G$ is the average transmission value of the green filter between $\lambda_1$ and $\lambda_h$. By substituting $\in_B(\lambda)$ from equation (3) into equation (6), the expression becomes:

$$E_C = 2\overline{F}_G \in_{BG} \quad (7)$$

(NOTE: the portion of the integral in equation (3) between $\lambda_h$ and $\lambda_2$ is zero). Since the solution is assumed to be symmetrical about $\lambda_1$:

$$E_C = 2\overline{F}_G \in_{BG} = 2\overline{F}_B \in_{GB}; \quad (8)$$

where $\overline{F}_B$ is the average transmission value of the blue filter between $\lambda_1$ and $\lambda_1$.

The relationships represented in equation (8) yield the following equations that describe the out-of-band irradiances $\in_{BG}$ and $\in_{GB}$ as a function of the total irradiance measured while the light is being filtered by both filters $E_C$ (e.g., the measurement taken at operation 166 of method 144):

$$\varepsilon_{BG} = \frac{E_C}{2\overline{F}_G}; \text{ and} \quad (9)$$

$$\varepsilon_{GB} = \frac{E_C}{2\overline{F}_B}. \quad (10)$$

The average irradiances ($\overline{F}_G$ and $\overline{F}_B$) are constant values that can be determined from the specifications of the implemented filters.

Equations (9) and (10) can be combined with the terms of equations (3) and (4) to produce the following relationships:

$$E_B = \varepsilon_{BB} + \frac{E_C}{2\overline{F}_G}; \text{ and} \quad (11)$$

$$E_G = \frac{E_C}{2\overline{F}_B} + \varepsilon_{GG}, \quad (12)$$

which can also be expressed as:

$$\varepsilon_{BB} = E_B - \frac{E_C}{2\overline{F}_G}; \text{ and} \quad (13)$$

$$\varepsilon_{GG} = E_G - \frac{E_C}{2\overline{F}_B}. \quad (14)$$

Thus, returning again to FIG. 9, in one embodiment, $\in_{BB}$, $\in_{GG}$, $\in_{BG}$, and $\in_{GB}$ are determined at operation 172 from the measurements made at operations 150, 158, and 166 based on equations (9), (10), (13), and (14).

At an operation 174, the determinations of made at operation 172 are leveraged with the measurements made at operations 152, 154, 160, 162, 168, and 170 to determine a correction that accounts for the overlap between the wavelength response functions of the blue and green photodiodes. The correction includes determining a set of coefficients that can be used to determine corrected values for the irradiance within the blue and green portions of the spectrum based on the output currents of the blue and green photodiodes. These coefficients can be expressed as a matrix $$\begin{pmatrix} \alpha & \beta \\ \gamma & \delta \end{pmatrix}$$

that is a solution to the equation:

$$\begin{pmatrix} \varepsilon_B \\ \varepsilon_G \end{pmatrix} = \begin{pmatrix} \alpha & \beta \\ \gamma & \delta \end{pmatrix} \cdot \begin{pmatrix} i_B \\ i_G \end{pmatrix}; \quad (15)$$

where $i_B$ represents the output current of blue photodiode and $i_G$ represents the output current of the green photodiode.

Assuming that the output current of a photodiode can be expressed as $I=R^*\in$; where I represents the output current, R represents the photodiode response, and $\in$ represents the irradiance received by the photodiode, the output current of the blue photo diode in response to the filtered blue illumination ("$i_{BB}$") obtained at operation 152 can be expressed as:

$$i_{BB} = \frac{1}{(\lambda_1 - \lambda_0)} \int_{\lambda_0}^{\lambda_1} R_B(\lambda) \varepsilon_B(\lambda) d\lambda + \frac{1}{(\lambda_2 - \lambda_1)} \int_{\lambda_1}^{\lambda_2} R_B(\lambda) \varepsilon_B(\lambda) d\lambda. \quad (16)$$

Assuming that the response of the blue photodiode, $R_B(\lambda)$, is approximately constant over each of the spectral ranges ($\lambda_0$-$\lambda_1$ and $\lambda_1$-$\lambda_2$), the integrals in equation (16) can be rewritten as:

$$\frac{1}{(\lambda_1 - \lambda_0)} \int_{\lambda_0}^{\lambda_1} R_B(\lambda) \varepsilon_B(\lambda) d\lambda = A\varepsilon_{BB}; \text{ and} \quad (17)$$

$$\frac{1}{(\lambda_2 - \lambda_1)} \int_{\lambda_1}^{\lambda_2} R_B(\lambda) \varepsilon_B(\lambda) d\lambda = B\varepsilon_{BG}. \quad (18)$$

So:

$$i_{BB} = A\varepsilon_{BB} + B\varepsilon_{BG}; \quad (19)$$

where A and B are proportionality constants. This equation expresses a contribution to $i_{BB}$ of irradiance (at operation 152) due to illumination that passes through the blue filter within the blue portion of the spectrum ($\in_{BB}$) and illumination that passes through the blue filter within the green portion of the spectrum ($\in_{BG}$). By a similar technique, the output current of the green photodiode in response to illumination that has been filtered by the blue filter ("$i_{GB}$") (obtained at operation 154) can be expressed as:

$$i_{GB} = \Gamma\varepsilon_{BB} + \Delta\varepsilon_{BG}; \quad (20)$$

where $\Gamma$ and $\Delta$ represent proportionality constants. Similarly, the output current of the blue diode in response to illumination filtered by the green filter ("$i_{BG}$") (obtained at operation 160), and the output current of the green diode in response to illumination filtered by the green filter ("$i_{GG}$") (obtained at operation 162) can be expressed as:

$$i_{BG} = A\in_{GB} + B\in_{GG}; \text{ and} \quad (21)$$

$$i_{GG} = G\in_{GB} + D\in_{GG}, \text{ respectively}. \quad (22)$$

Taken together, equations (19) and (20) can be rewritten in matrix form as:

$$\begin{pmatrix} i_{BB} \\ i_{GB} \end{pmatrix} = \begin{pmatrix} A & B \\ \Gamma & \Delta \end{pmatrix} \cdot \begin{pmatrix} \varepsilon_{BB} \\ \varepsilon_{BG} \end{pmatrix}, \quad (23)$$

and equations (21) and (22) can be rewritten as:

$$\begin{pmatrix} i_{BG} \\ i_{GG} \end{pmatrix} = \begin{pmatrix} A & B \\ G & D \end{pmatrix} \cdot \begin{pmatrix} \varepsilon_{GB} \\ \varepsilon_{GG} \end{pmatrix}, \quad (24)$$

Since we are assuming the overlap of wavelength response functions and transmission functions to be approximately symmetrical about $\lambda_1$, it can be assumed that A=A, B=B, $\Gamma$=G, and A=D. Thus, matrix equations (23) and (24) yield a system of four equations with four unknowns (the proportionality constants A, B, $\Gamma$, and $\Delta$). This enables the unknowns, the proportionality constants to be determined.

Referring back to equations (23) and (24), the proportionality constants A, B, $\Gamma$, and A are now known, but the equations (23) and (24) return a current as a function of irradiance. These equations can be rewritten to provide irradiance as a function of current by inverting the equations, which yields:

$$\begin{pmatrix} \varepsilon_{BB} \\ \varepsilon_{BG} \end{pmatrix} = \begin{pmatrix} \alpha & \beta \\ \gamma & \delta \end{pmatrix} \cdot \begin{pmatrix} i_{BB} \\ i_{GB} \end{pmatrix}; \text{ and} \quad (25)$$

$$\begin{pmatrix} \varepsilon_{GB} \\ \varepsilon_{GG} \end{pmatrix} = \begin{pmatrix} \alpha & \beta \\ \gamma & \delta \end{pmatrix} \cdot \begin{pmatrix} i_{BG} \\ i_{GG} \end{pmatrix}, \text{ where} \quad (26)$$

$$\begin{pmatrix} A & B \\ \Gamma & \Delta \end{pmatrix}^{-1} = \begin{pmatrix} \alpha & \beta \\ \gamma & \delta \end{pmatrix}. \quad (27)$$

Of course, in practical usage, illumination in the green and blue portions of the spectrum will not reach the photodiodes separately, so only two currents will be available. By combining equations 25 and 26, a matrix equation that provides for the correction to be determined at operation 174 is as follows:

$$\begin{pmatrix} \varepsilon_B \\ \varepsilon_G \end{pmatrix} = \begin{pmatrix} \alpha & \beta \\ \gamma & \delta \end{pmatrix} \cdot \begin{pmatrix} i_B \\ i_G \end{pmatrix}, \quad (28)$$

where $\alpha$, $\beta$, $\gamma$, and $\delta$ are the constants determined according to the derivation provided above. This correction can be applied to the output currents of the blue diode and the green diode to enhance the accuracy of the irradiances determined therefrom.

It should be appreciated that method 144 is merely intended as one example of determining a set of corrections and that other methods may be employed to determine corrections for overlaps between the wavelength response functions of the individual photodiodes included in an illumination sensor. For example, a simplified set of corrections would enable determination of the intensity of the illumination in the wavelength ranges by multiplying the output signals of individual photodiodes (or individual sets of photodiodes in the embodiment in which an array of diodes is implemented) by appropriate proportionality constants. For example, rather than being in the form of the matrix equation presented above, the correction for all three of the photodiodes may be of the following form:

$$\in_B = \rho_B i_B, \quad (29a)$$

$$\in_G = \rho_G i_G, \text{ and} \quad (29b)$$

$$\in_R = \rho_R i_R; \quad (29c)$$

where $\rho_B$ represents the proportionality constant for the blue photodiode/portion of the spectrum, $\rho_G$ represents the proportionality constant for the green photodiode/portion of the spectrum, and $\rho_R$ represents the proportionality constant for the red photodiode/portion of the spectrum. Such a set of equations may be determined, for example, based upon experimentally collected data at the time of manufacture of the illumination sensor.

As should be appreciated from the derivation of the correction represented in equation (28), no matter what form the correction takes (e.g., equation (28), equations (29a)-(29c), etc.), the assumptions made in determining the correction regarding the nature of the illumination source (e.g., a blackbody source in the derivation of equation (28)) will render the results generated by a given correction inaccurate when the illumination sensor receives radiation from a different type of radiation source (e.g., a colored LED, color filtered illumination, etc.).

Referring back to FIG. 1, in order to account for inaccuracies caused by assumptions about the illumination source made in determining a correction for overlap between the wavelength functions of photodiodes in illumination sensor 30, in one embodiment, storage module 22 stores a set of corrections that correspond to different types of illumination sources. In this embodiment, correction module 38 is configured to determine the type of illumination source that is emitting the ambient radiation based on the one or more output signals generated by illumination sensor 30, and to implement a correction from the set of corrections stored in storage module 22 that corresponds to the determined type of illumination source. The illumination source types may include, for example, a white light source (e.g., a blackbody source), a blue light source, a green light source, a red light source, and/or other light source types.

In one embodiment in which correction module 28 determines the illumination source type and implements the corresponding correction, correction module 38 is disposed in substantially continuous communication with sensor 14 (e.g., within portable device 46 illustrated in FIG. 2). In this embodiment, correction module 38 determines the illumination source type of the illumination source emitting the ambient radiation in real time, or near real time, and implements the corresponding correction to the output signal(s) generated by illumination sensor 30 prior to storage within storage module 22. In another embodiment, correction module 38 is disposed in a processor remote from sensor 14 (e.g., in the host computer with which docking device 48 of FIG. 2 is connected), and determines the illumination source type of the illumination source based on information that has been downloaded to the remote processor.

Figure 10:
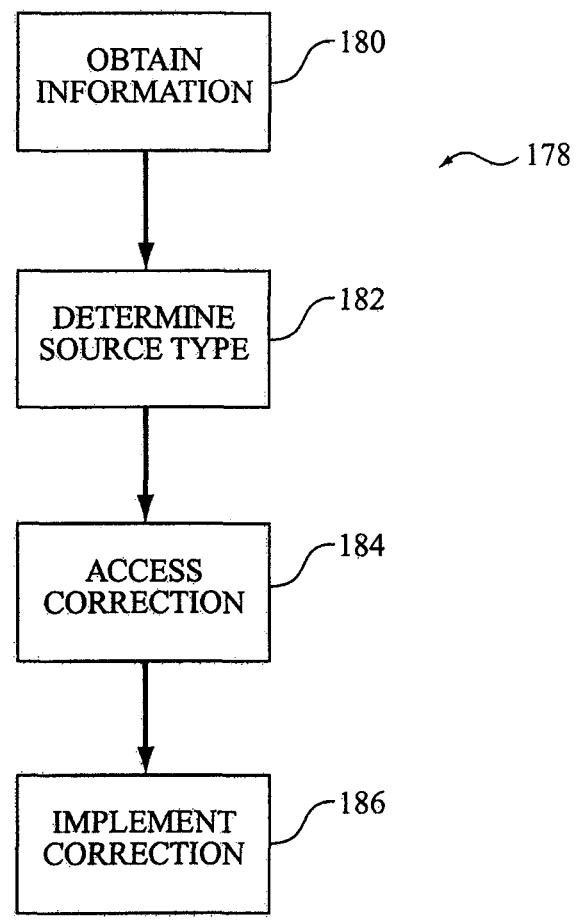
FIG. 10 illustrates a method of correcting for overlapping wavelength response functions of illumination sensors, in accordance with one embodiment of the invention.

FIG. 10 illustrates a method 178 of correcting for overlapping wavelength response functions of illumination sensors. Although the operations of method 178 are discussed below with respect to the components of system 10 described above and illustrated in FIGS. 1-4, it should be appreciated that this is for illustrative purposes only, and that method 178 may be implemented with alternative components and/or systems without departing from the scope of this disclosure.

At an operation 180, information related to one or more output signals that convey information related to the intensity of ambient illumination within two or more wavelength ranges is obtained. In one embodiment, the one or more output signals are generated by an illumination sensor similar to illumination sensor 30, described above and illustrated in FIG. 1. Obtaining the information at operation 180 may include receiving the output signals as they are generated, receiving information that represents the output signals as they are generated, accessing stored information that represents the one or more output signals, and/or otherwise obtaining the information.

At an operation 182, an illumination source type of an illumination source emitting the ambient illumination is determined based on one or more comparisons between the intensities of the ambient illumination within individual ones of the two or more wavelength ranges. In one embodiment, operation 182 is performed by a correction module similar to correction module 38 illustrated in FIG. 1 and described above.

At an operation 184, a correction is accessed from a set of stored corrections that correspond to a plurality of illumination source types. The accessed correction corresponds to the determined illumination source type. In one embodiment, the set of stored corrections is stored within a storage module similar to storage module 22, illustrated in FIG. 1 and described above. Operation 184 may be executed by a correction module similar to correction module 38, illustrated in FIG. 1 and described above.

At an operation 186, the accessed correction is implemented in determining the intensities of the ambient illumination within the two or more wavelength ranges based on the information related to the one or more output signals obtained at operation 180. In one embodiment, operation 186 is performed by a processor similar to processor 18, illustrated in FIG. 1 and described above.

Figure 11:
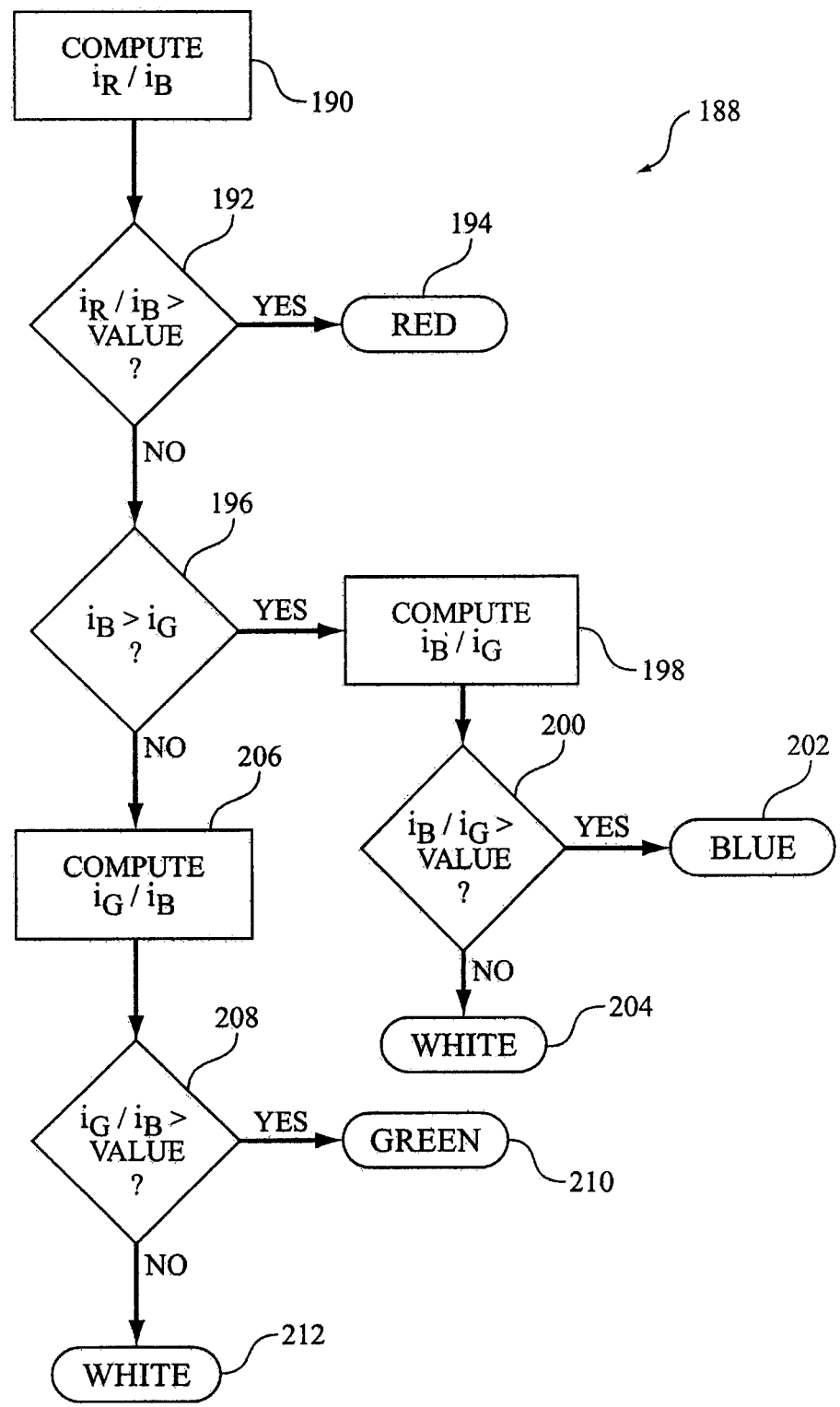
FIG. 11 illustrates a method of comparing the intensity of ambient illumination within two or more wavelength ranges to determine an illumination source type of the illumination source emitting the ambient illumination, in accordance with one embodiment of the invention.

FIG. 11 illustrates a method 188 of comparing the intensity of ambient illumination within two or more wavelength ranges to determine an illumination source type of the illumination source emitting the ambient illumination. In one embodiment, method 188 can be implemented as operation 182 in method 178, illustrated in FIG. 10 and described above. However, the implementation of method 188 in other contexts is also contemplated. As used herein, for example with respect to method 188, the comparing of intensity refers to comparisons of any measurement of incident illumination that is substantially related to intensity (e.g., irradiance, illuminance, etc.).

In one embodiment, the two or more wavelength ranges include a first wavelength range (e.g., corresponding to the blue portion of the spectrum), a second wavelength range (e.g., corresponding to the green portion of the spectrum), and a third wavelength range (e.g., corresponding to the red portion of the spectrum). The one or more output signals include a first output signal generated by a sensor with a wavelength response function that corresponds substantially to the first wavelength range, a second output signal generated by a sensor with a wavelength response function that corresponds substantially to the second wavelength range, and a third output signal generated by a sensor with a wavelength response function that corresponds substantially to the third wavelength range.

Method 188 includes an operation 190, at which a comparison is made between the intensity of ambient illumination within the first wavelength range and the intensity of ambient illumination within the second wavelength range. In one embodiment, this comparison includes determining a ratio between the magnitude of the third output signal and the first output signal (e.g., $i_R/i_B$). The determined ratio is then compared with a predetermined value at an operation 192. If it is determined that the ratio determined at operation 188 is greater than the predetermined value, then the illumination source is determined to be of a type that primarily emits illumination within the third wavelength range (e.g., a red light source) at an operation 194.

If, at operation 192, it is determined that the ratio determined at operation 188 is less than the predetermined value, then method 188 proceeds to an operation 196. At operation 196, a comparison is made between the intensity of ambient illumination within the first wavelength range and the intensity of ambient illumination within the second wavelength range. In one embodiment, this comparison includes determining whether the magnitude of the first output signal is greater than the magnitude of the second output signal (e.g., $i_B > i_G$). If the magnitude of the first output signal is greater than the magnitude of the second output signal, then a second comparison is made between the intensities of ambient illumination within the first and second wavelength ranges is made at an operation 198. The comparison made at operation 198 includes determining a ratio between the magnitude of the first output signal and the magnitude of the second output signal (e.g., $i_B/i_G$). The determined ration is then compared with another predetermined value at an operation 200.

If the ratio determined at operation 198 is determined to be greater than the predetermined value at operation 200, then the illumination source type of the illumination source emitting the ambient illumination is determined to be of a type that primarily emits illumination within the first wavelength range (e.g., a blue light source) at an operation 202. If the ratio determined at operation 198 is determined to be less than the predetermined value at operation 200, then the ambient illumination source is determined to be of a type that emits illumination with relative uniformity across each of the first, second, and third wavelength ranges (e.g., a white light source) at an operation 204.

If, at operation 196 it is determined that the magnitude of the first output signal is less than the magnitude of the second output signal (e.g., $i_B < i_G$), then method 144 proceeds to an operation 206, at which a yet another comparison is made between the intensity of ambient illumination within the first wavelength range and the intensity of ambient illumination within the second wavelength range. In one embodiment, this comparison includes determining a ratio between the magnitude of the second output signal and the magnitude of the first output signal (e.g., $i_G/i_B$). The determined ration is then compared with yet another predetermined value at an operation 208.

If the ratio determined at operation 206 is determined to be greater than the predetermined value at operation 208, then the illumination source type of the illumination source emitting the ambient illumination is determined to be of a type that primarily emits illumination within the second wavelength range (e.g., a green light source) at an operation 210. If the ratio determined at operation 206 is determined to be less than the predetermined value at operation 208, then the ambient illumination source is determined to be of a type that emits illumination with relative uniformity across each of the first, second, and third wavelength ranges (e.g., a white light source) at an operation 212.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it should be understood that the present invention contemplates that, to the extent possible, one or more features of any embodiment can be combined with one or more features of any other embodiment.

What is claimed is:

1. A system configured to monitor ambient illumination experienced by a subject, the system comprising a wearable piece, the wearable piece comprising:
    an illumination sensor configured to monitor an intensity of ambient illumination within two or more wavelength ranges by generating one or more output signals that convey information related to the intensity of ambient illumination within the two or more wavelength ranges;
    a timer configured to indicate the passage of periods of time;
    a motion sensor configured to monitor movement of the subject by generating one or more output signals that convey information related to movement of the subject;
    a storage module configured to:
        store information related to the intensity of ambient illumination within the two or more wavelength ranges, as conveyed by the one or more output signals, in separate sets of data that correspond to individual periods of time; and
        store information related to movement of the subject, as conveyed by the one or more output signals generated by the motion sensor, during the individual periods of time; and
    a communication interface configured to facilitate communication of the sets of data and the information related to movement of the subject to an external processor;
    wherein, at least the illumination sensor, the timer, the motion sensor, the storage module, and/or the communication interface is portable to be carried by the subject.

2. The system of claim 1, further comprising a strap that engages an extremity of the subject, wherein the illumination sensor, the timer, and the storage module are carried on the strap.

3. The system of claim 1, further comprising a proximity sensor configured to monitor whether or not the subject is wearing the system by generating an output signal that indicates whether or not the subject is proximate to the proximity sensor.

4. The system of claim 1, wherein the two or more wavelength ranges comprise three wavelength ranges.

5. The system of claim 4, wherein the three wavelength ranges include a first wavelength range corresponding to red, a second the wavelength range corresponding to green, and a third wavelength range corresponding to blue.

6. The system of claim 1, wherein the information stored by the storage module enables a determination of photon flux for individual ones of the two or more wavelength ranges during individual periods.

7. The system of claim 1, wherein the illumination sensor comprises one or both of (i) an array of photodiodes, the photodiodes included in the array comprise, for a given one of the two or more wavelength ranges, one or more photodiodes capable of monitoring the intensity of ambient illumination in the given one of the two or more wavelength ranges, or (ii) a spectrophotometer.

8. The system of claim 1, wherein the external processor comprises an illumination score module configured to determine, from the intensities of ambient illumination within the two or more wavelength ranges, a metric indicating a resetting effect of ambient illumination on a circadian phase of the subject.

9. The system of claim 1, wherein the motion sensor comprises one or more of an actimeter, a position sensor, a displacement sensor, or an accelerometer.

10. A system configured to monitor ambient illumination experienced by a subject, the system comprising a wearable piece, the wearable piece comprising:
    means for monitoring an intensity of ambient illumination within two or more wavelength ranges by generating one or more output signals that convey information related to the intensity of ambient illumination within the two or more wavelength ranges;
    means for determining the passage of periods of time;
    means for monitoring movement of the subject by generating one or more output signals that convey information related to movement of the subject;
    means for storing information related to the intensity of ambient illumination within the two or more wavelength ranges, as conveyed by the one or more output signals, in separate sets of data that correspond to individual periods of time;
    means for storing information related to movement of the subject, as conveyed by the one or more output signals generated by the means for monitoring movement, during the individual periods of time; and
    means for facilitating communication of the sets of data and the information related to movement of the subject to an external processor;
    wherein, at least the means for monitoring an intensity of ambient illumination, the means for determining the passage of periods of time, the means for monitoring movement, the means for storing information related to movement, and/or the means for storing information related to the intensity of ambient illumination are portable to be carried by the subject.

11. The system of claim 10, further comprising a strap that engages an extremity of the subject, wherein the means for monitoring an intensity of ambient illumination, the means for monitoring movement, the means for determining the passage of periods of time, the means for storing information related to movement, and the means for storing information related to the intensity of ambient illumination are carried on the strap.

12. The system of claim 10, further comprising means for monitoring whether or not the subject is wearing the system.

13. The system of claim 10, wherein the two or more wavelength ranges comprise three wavelength ranges.

14. The system of claim 13, wherein the three wavelength ranges include a first wavelength range corresponding to red, a second the wavelength range corresponding to green, and a third wavelength range corresponding to blue.

15. The system of claim 10, wherein the information stored by the means for storing information related to the intensity of ambient illumination enables a determination of photon flux for individual ones of the two or more wavelength ranges during individual periods.

16. The system of claim 10, wherein the external processor comprises means for determining, from the intensities of ambient illumination within the two or more wavelength ranges, a metric indicating a resetting effect of ambient illumination on the circadian phase of the subject.

* * * * *